US011430567B2

(12) United States Patent
Johnstone et al.

(10) Patent No.: US 11,430,567 B2
(45) Date of Patent: Aug. 30, 2022

(54) METHODS FOR TRACKING AND RESPONDING TO MENTAL HEALTH CHANGES IN A USER

(71) Applicant: Social Health Innovations, Inc., Kent, DE (US)

(72) Inventors: Amanda Johnstone, Youngtown (AU); Oliver Rozynski, Youngtown (AU)

(73) Assignee: Social Health Innovations, Inc., Dover, DE (US)

( * ) Notice: Subject to any disclaimer, the term of this patent is extended or adjusted under 35 U.S.C. 154(b) by 199 days.

(21) Appl. No.: 16/424,299

(22) Filed: May 28, 2019

(65) Prior Publication Data

US 2020/0152323 A1    May 14, 2020

Related U.S. Application Data

(63) Continuation of application No. 15/233,732, filed on Aug. 10, 2016, now abandoned.

(60) Provisional application No. 62/203,083, filed on Aug. 10, 2015.

(51) Int. Cl.
*G16H 40/63* (2018.01)
*G06Q 50/00* (2012.01)
*G06F 16/22* (2019.01)
*G16Z 99/00* (2019.01)

(52) U.S. Cl.
CPC ......... *G16H 40/63* (2018.01); *G06F 16/2228* (2019.01); *G06Q 50/01* (2013.01); *G16Z 99/00* (2019.02)

(58) Field of Classification Search
CPC . G06F 19/3406; G06F 16/2228; G16H 40/63; G06Q 50/01
See application file for complete search history.

(56) References Cited

U.S. PATENT DOCUMENTS

| 2008/0098074 A1* | 4/2008 | Hurling | G16H 20/00 |
| | | | 709/206 |
| 2010/0180289 A1* | 7/2010 | Barsook | G11B 27/005 |
| | | | 725/29 |
| 2010/0245358 A1* | 9/2010 | Heywood | G16H 10/60 |
| | | | 345/440 |

(Continued)

OTHER PUBLICATIONS

Yuan Gao et al., "What Does Touch Tell Us about Emotions in Touchscreen-Based Gameplay?" ACM Transactions on Computer-Human Interaction vol. 19 Issue Dec. 4, 2012 Article No. 31pp. 1-30https://doi.org/10.1145/2395131.2395138 (Year: 2012).*

*Primary Examiner* — Joshua B Blanchette
(74) *Attorney, Agent, or Firm* — Run8 Patent Group, LLC; Peter Miller; Ryan D. Smith

(57) ABSTRACT

One variation of a method for tracking and responding to mental health changes in a user, the method includes: rendering a graphical object within a graphical user interface; indexing an emotion value assigned to the graphical object through a spectrum of emotion values according to a direction of an input into the graphical user interface; within the graphical user interface, updating the graphical object to visually correspond to the emotion value assigned to the graphical object; recording submission of a final emotion value through the graphical user interface; and in response to the final emotion value equaling a trigger value, distributing a prompt to monitor the user to an external entity.

19 Claims, 9 Drawing Sheets

(56) References Cited

U.S. PATENT DOCUMENTS

| | | | | |
|---|---|---|---|---|
| 2012/0303706 A1* | 11/2012 | Young | ............... | G06Q 50/01 |
| | | | | 709/204 |
| 2014/0195255 A1* | 7/2014 | Ghosh | ............... | G16H 20/60 |
| | | | | 705/2 |
| 2014/0324719 A1* | 10/2014 | Canal | ............... | G06F 16/958 |
| | | | | 705/319 |
| 2015/0287403 A1* | 10/2015 | Holzer Zaslansky | ... | G10L 21/10 |
| | | | | 704/231 |
| 2015/0324532 A1* | 11/2015 | Jones | ............... | G16H 40/67 |
| | | | | 705/2 |
| 2016/0259535 A1* | 9/2016 | Fleizach | ............ | G06F 3/04883 |
| 2016/0261675 A1* | 9/2016 | Block | ............... | G06F 3/0481 |

* cited by examiner

METHODS FOR TRACKING AND RESPONDING TO MENTAL HEALTH CHANGES IN A USER

CROSS-REFERENCE TO RELATED APPLICATIONS

This application is a continuation of U.S. patent application Ser. No. 15/233,732, filed on 10 Aug. 2016, which claims the benefit of U.S. Provisional Application No. 62/203,083, filed on 10 Aug. 2015, each of which is incorporated in its entirety by this reference.

TECHNICAL FIELD

This invention relates generally to the field of mental health and more specifically to a new and useful method for tracking and responding to mental health changes in the field of mental health.

DESCRIPTION OF THE EMBODIMENTS

The following description of the embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. Method

Figure 1:
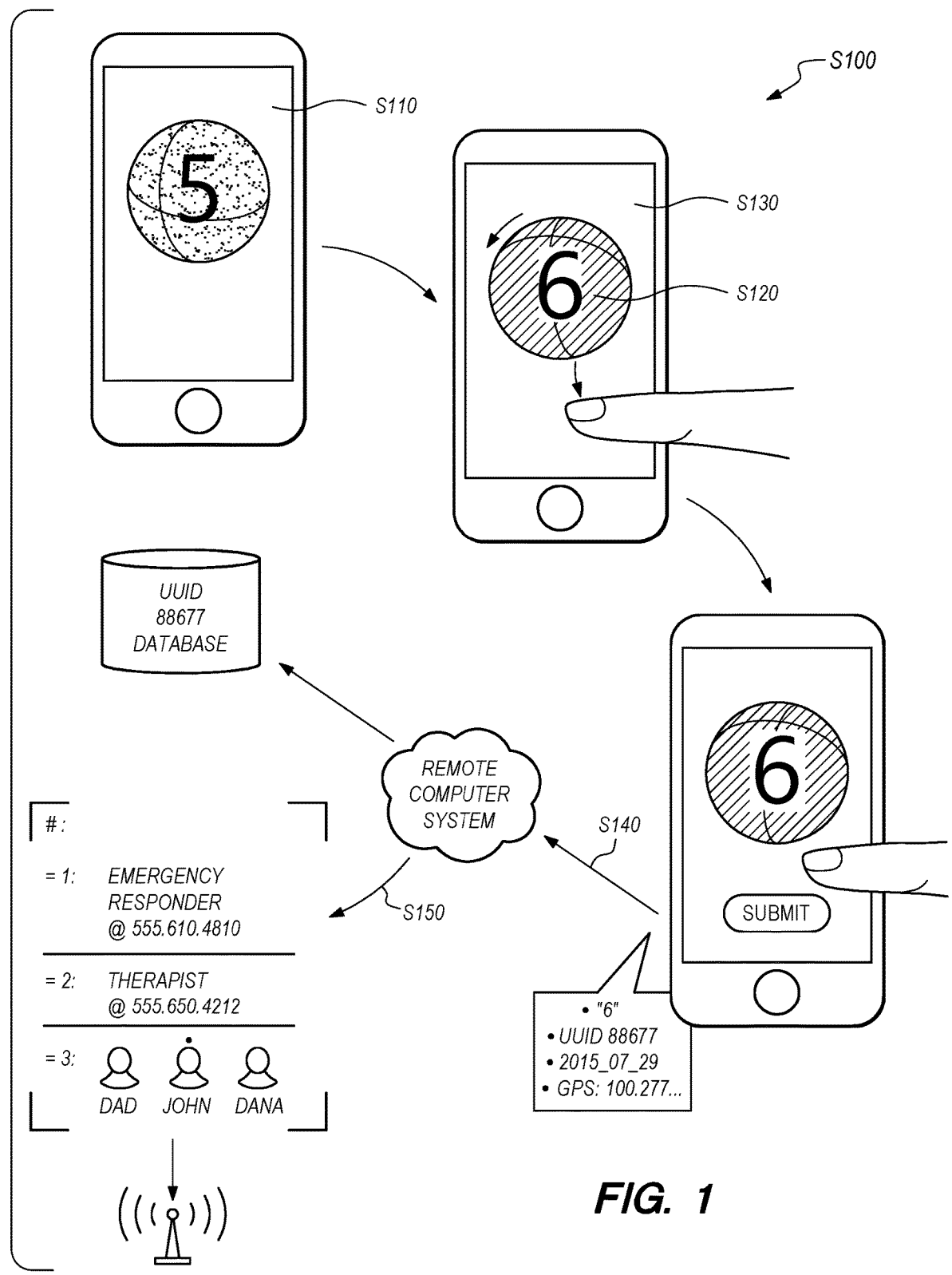
FIG. 1 is a flowchart representation of a method.

As shown in FIG. 1, a method S100 for tracking and responding to mental health changes includes: rendering a graphical object within a graphical user interface in Block S100; in response to a swipe input over the graphical user interface by a user, indexing an emotion value represented on the graphical object in Block S120; updating a color value and a virtual viscosity represented on the graphical object based on the emotion value represented on the graphical object in Block S130; in response to an input on the graphical user interface, submitting the emotion value to an external entity in Block S150; and in response to the emotion value equaling a trigger value, prompting the external entity to contact the user in Block S150.

As shown in FIG. 1, one variation of the method S100 includes: rendering a graphical object within a graphical user interface in Block S100; indexing an emotion value assigned to the graphical object through a spectrum of emotion values according to a direction of an input into the graphical user interface in Block S120; within the graphical user interface, updating the graphical object to visually correspond to the emotion value assigned to the graphical object in Block S130; recording submission of a final emotion value through the graphical user interface in Block S140; and in response to the final emotion value equaling a trigger value, distributing a prompt to monitor the user to an external entity in Block S150.

Figure 6:
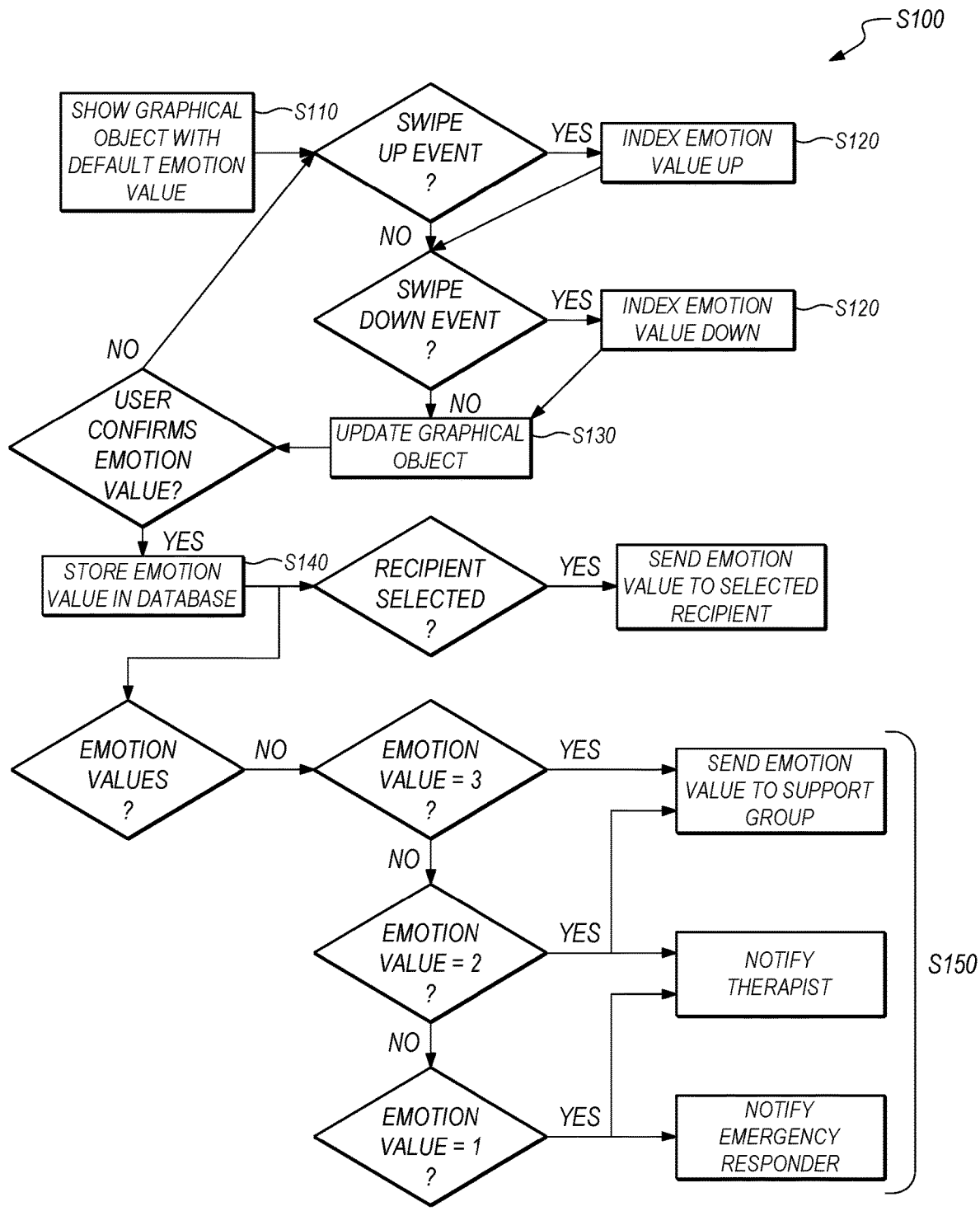
FIG. 6 is a flowchart representation of one variation of the method.

As shown in FIG. 6, another variation of the method S100 includes: rendering a graphical object within a graphical user interface in Block S100; indexing an emotion value assigned to the graphical object according to a direction of a swipe input over the graphical object within the graphical user interface in Block S120; updating a color value and a virtual viscosity of the graphical object to correspond to the emotion value assigned to the graphical object in Block S130; distributing a dynamic visual object, representing the graphical object in a color value and a virtual viscosity corresponding to a final emotion value selected by the user, to a first recipient elected by the user in Block S150; in response to the final emotion value equaling a first trigger value, prompting a second recipient to contact the user in Block S150; and in response to the final emotion value equaling a second trigger value representing a less content state of the user than the first trigger value, distributing the final emotion value to a mental health entity in Block S150.

Figure 9:
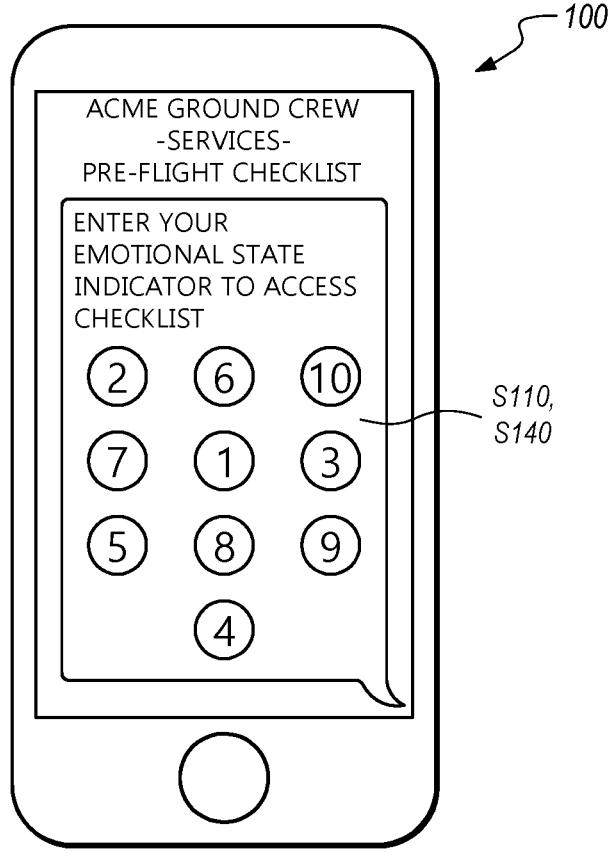
FIG. 9 is a graphical representation of one variation of the method.

As shown in FIGS. 6 and 9, yet another variation of the method S100 includes: at a computing device linked to the user, receiving an emotion value, on a spectrum of emotion values, selected by the user in Block S140; recording the emotion value in a database of emotion values entered by the user in Block S150; enabling access to a process on the computing device in response to receipt of the emotion value in Block S150; and, in response to the emotion value equaling a trigger value corresponding to a low state of contentment, distributing a second prompt to a mental health representative to monitor the user in Block S150.

2. Applications

Generally, Blocks of the method S100 can be executed on a user's computing device and/or within a computer network to track the user's emotional state—such as the user's current mood, general feeling, perceived emotional health, perceived relationship condition, and/or perceived financial condition, etc.—through simple gestures entered manually by the user over time and to selectively prompt others to support the user based on quantitative or qualitative values entered by the user to represent the user's emotional state. In particular, Blocks of the method S100 can be implemented by a standalone native mental health application, a native employment application issued by an employer, an alternate lock screen, and/or an alternate keyboard, etc. (hereinafter a "graphical user interface") executing on a smartphone, tablet, or other computing device owned by or assigned to a user. At various instances over time, the user can access the graphical user interface to submit an emotion value representing the user's current emotional state, such as in response to a prompt automatically issued by the computing device or in order to access additional content or functions on the computing device.

In one example, a computing device executing Blocks of the method S100 S100 renders a virtual sphere (i.e., a "graphical object") on a touchscreen, moves the virtual sphere according to swipe inputs entered by the user over the touchscreen, and updates an emotion value represented by (e.g., displayed on), a color of, and/or a geometry of the virtual sphere in response to each swipe input entered by the user. The user can then confirm the emotion value represented by the virtual sphere, such as by selecting a confirm region of the touchscreen; and the computing device can upload the final emotion value to a remote database, push the emotion value to a user-elected recipient, and/or distribute prompts to friends, family, therapists, emergency responders, etc. based on the emotion value, such as if the emotion value equals one of a preset trigger value associated with such prompts.

A computing device (e.g., a smartphone, tablet, augmented or virtual reality headset, heads-up or eyes-up display, monitoring device, wearable sensor, implanted device, smart glasses, or smartwatch, etc.) executing Blocks of the method S100 can therefore enable a user to quickly and seamlessly enter a qualitative or quantitative value representing her perceived emotional state or perceived emotional wellbeing and then selectively engage others to support the user when emotion values entered by the user indicate that the user may be in need of such support. For example, an alternate keyboard executing Blocks of the method S100 can enable the user to send a graphical object (e.g., a dynamic virtual sphere, a GIF, an emoticon) representing the user's perceived emotional state to one selected recipient through a native text messaging application; the alternate keyboard can also store the emotion value selected by the user for the graphical object, prompt a friend or family member of the user other than the selected recipient to contact or otherwise support the user if the selected emotion value equals a low trigger value, and prompt yet another entity (e.g., a therapist, an emergency responder) to contact or monitor the user if the selected emotion value equals an even lower trigger value. In another example, a computing device (e.g., a smartphone or tablet) can incorporate Blocks of the method S100 into a lock screen, prompt the user to both enter a passcode and to select (or enter) an emotion value in order to unlock the computing device, record a selected emotion value upon receipt of a correct passcode, and then selectively prompt friends, family, a therapist, or an emergency responder, etc. to connect with the patient if the selected emotion value is sufficiently low or equals corresponding trigger values. Therefore, the method S100 can be: implemented in a consumer application (e.g., a communication application) or process to enable a user enter emotion values, to track the user's emotion values over time, and to automatically prompt other humans to support the user; and/or implemented in an enterprise application to track the emotional state of employees, to gate (i.e., limit) access to sensitive processes or information when the user's selected emotion values are sufficiently low, and to automatically prompt involve a mental health professional to monitor the user when such need is indicated by the user's selected emotion values.

Blocks of the method S100 can be implemented by a computing device (e.g., a smartphone, a tablet, a smart watch), within a computer system, across a computer network and can be hosted by a mental health clinic, a hospital, an employer, a school, a government or agency, a military or defense force, or any other entity to collect simple (e.g., basic) mental health-related data manually entered by one or more users within a user population. However, Blocks of the method S100 can be executed on any other computer system and in conjunction with any other entity or service.

3. Emotion Value

Blocks of the method S100 collect, handle, and respond to emotion values entered by the user through a computing device. Generally, an emotion value can represent the user's perceived overall emotional state, perceived emotional wellbeing, perceived intensity of a mood, or emotional stability, etc. at a particular moment in time in a single quantitative or qualitative value that can be simply and quickly entered into the computing device by the user.

In this implementation, the computing device: maintains a range of quantitative emotion values from "1" through "10," inclusive; indexes through this range of values according to inputs into the computing device; and renders a single current emotion value from this range on the graphical object (e.g., a virtual sphere) shown within the graphical user interface at any one time, as shown in FIG. 1. For example, each emotion value within the range of emotion values can correspond to a particular response (or particular response range) on a continuum of responses, including: "emergency" for an emotion value of "1"; "need support" for an emotion value of "2"; "very poor" for an emotion value of "3"; "poor" for an emotion value of "4"; "average" for an emotion value of "5"; "ok" for an emotion value of "6"; "good" for an emotion value of "7"; "great" for an emotion value of "8"; "excellent" for an emotion value of "9"; and "extraordinary" for an emotion value of "10" (or vice versa). In this example and as described below, the computing device executing Blocks of the method S100 can index through these quantitative emotion values in order based on a direction of each swipe input entered into the computing device by the user. In particular, by first presenting the emotion value "5" in a virtual sphere shown in the graphical user interface on a display of the computing device, indexing toward "1" in response to each swipe-down or (scroll-down) input event at the computing device, and indexing toward "10" in response to each swipe-up or (scroll-up) input event at the computing device, the computing device can enable the user to reach any emotion value representing her current emotional state with as little as five simple and identical swipe (or scroll) inputs into the computing device. The computer system can also update a color of, a virtual viscosity of, and/or a number value shown on a graphical object (e.g., a virtual sphere) rendered in the graphical user interface to represent the current quantitative emotion value selected by the user, as described below and shown in FIG. 2.

In another example, an augmented reality headset, a virtual reality headset, or a pair of smart glasses—executing Blocks of the method S100 and worn by a user—advances through the set of emotion values in response to a detected eye wink or head nod performed by the user wearing the computing device. In another example, a smartwatch—executing Blocks of the method S100 and worn by a user—advances through the set of emotion values in response to a detected raise of the user's hand. In yet another example, a smartphone or tablet—executing Blocks of the method S100 and carried by a user—advances forward through the set of emotion values in response to a detected tilt of the smartphone in a first direction and advances backward through the set of emotion values in response to a detected tilt of the smartphone in an opposite direction. Alternatively the smartphone can advance through the set of emotion values when the smartphone is shaken.

In another example, the computing device can present a text field within the graphical user interface and enable the user to type a single digit number (e.g., from "0" to "9")—corresponding to a quantitative emotion value—into the text field. Similarly, the graphical user interface can render a number pad with discrete input regions labeled "1" through "10" (or "0" through "9"), and the user can select one of these numbers to enter a quantitative emotion value. In one variation, Blocks of the method S100 are executed remotely, such as by a remote server or internal server within a network, upon receipt of a number value from a device issued to a user. For example, a user (e.g., an astronaut, naval pilot, or military personnel) can draft a SMS text message containing a numeric value at a satellite phone; the satellite phone can transmit the SMS text message to a remote server (e.g., hosted by a space agency or military group) that then processes the emotion value as described below in order to track and respond to the user's emotions over time. However, the method S100 can implement any other quantity of discrete integer values across any other range of values to represent the user's perceived emotional state.

In a similar implementation, a computing device executing Blocks of the method S100 implements a continuous range of quantitative emotion values, such as from "1.00" to "10.00," inclusive (e.g., 901 discrete possible values). For example, the computing device executing Blocks of the method S100 can implement a graphical slider bar and enable the user to move a slider to any of 901 positions between "1.00" (e.g., for "the worst") and "10.00" (e.g., for "the best") on the bar to enter a quantitative emotion value. Therefore, the computing device can enable the user to select an emotion value representing her current emotional state by moving the slider along the bar in a single left or right swipe input. In this example, the computing device can also update the graphical user interface rendered on the display of the computing device to show a quantitative value (e.g., "7.14" or "3.56") and/or a qualitative value (e.g., "great" or "poor") corresponding to each position of the slider on the bar as the user manipulates the slider.

Alternatively, a computing device executing Blocks of the method S100 can collect, handle, and respond to a range of qualitative emotion values. For example, the computing device can store a set of qualitative emotion values including: "my life is ending," "worst day ever," "things are terrible," "I've been worse," "I'm fine, "I'm good," "I'm great, "I'm excellent," and "I'm phenomenal." In this example, the computer system can index through this set of qualitative emotion values based on inputs entered by the user until the user reaches a relevant qualitative emotion value. For example, the computing device can render a slider bar within the graphical user interface, label discrete positions along the bar with one of each of these qualitative emotion values, and enable the user to select one of these qualitative emotion values by moving the slider along the bar to a corresponding position. Similarly, the computing device can populate a dropdown menu within the graphical user interface with each of these qualitative emotion values and enable the user to select one of these qualitative emotion values by navigating through the dropdown menu.

In yet another implementation, a computing device executing Blocks of the method S100 can automatically transform brainwave data received from a headset—such as an Electroencephalography (EEG) or Quantitative Electroencephalography (qEEG) headset containing one or more EEG electrodes—worn by a user into an emotion value.

Hereinafter, Blocks of the method S100 are described as collecting, handling, and responding to a set of quantitative emotion values spanning values "1" through "10," inclusive. However, the method S100 can implement any other range of quantitative or qualitative emotion values and can pair each emotion value within this range with any other suitable response, response type, or emotion intensity, etc. of the user at the time the emotion value was received.

4. Graphical Object and Graphical Object Updates

Block S100 of the method S100 recites rendering a graphical object within a graphical user interface; Block S120 of the method S100 recites, in response to a swipe input over the graphical user interface by a user, indexing an emotion value represented on the graphical object; and Block S130 of the method S100 recites updating a color value and a virtual viscosity represented on the graphical object based on the emotion value represented on the graphical object. Generally, the computing device can execute Block S100 to represent a current emotion value in the form of a graphical (i.e., visual) object; and the computing device can execute Blocks S120 and S130 to update the size, shape, geometry, color, and/or emotion value represented by (or on) the graphical object in response to an input entered by the user into the computing device.

Figure 2:
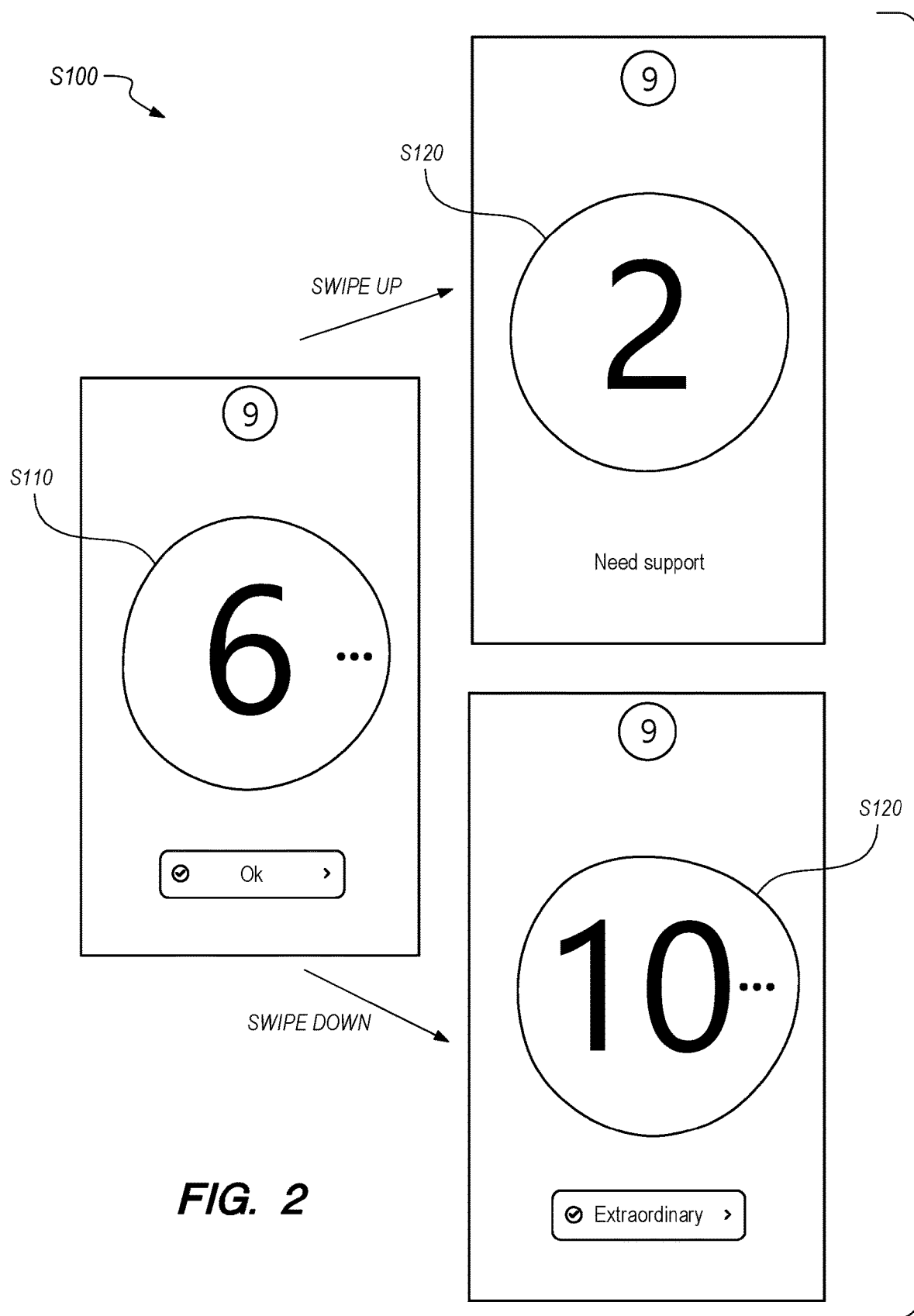
FIG. 2 is a flowchart representation of one variation of the method.

In one implementation, the computing device: renders the graphical object on a touchscreen in Block S110; and indexes through the range of emotion values in response to a swipe on the touchscreen and an index direction (i.e., increasing or decreasing) corresponding to the direction of the swipe on the touchscreen (e.g., up or down, respectively) in Block S120, as shown in FIG. 2. In this implementation, the computer system can index through the range of emotion values by a single step per discrete swipe input on the touchscreen in order to preserve deliberate emotion value changes and selections entered by the user. For example, in response to an upward swipe input over the graphical object, the computing device can index from an emotion value of "5" to an emotion value of "6"; similarly, in response to a downward swipe input over the graphical object, the computing device can index from an emotion value of "5" to an emotion value of "4." Alternatively, the computer system can implement an inertial model to scroll through the range of emotion values based on speed, distance, and/or direction of a swipe input in order to index through multiple emotion values within the range of emotion values in response to a single swipe input entered by the user in Block S120. The computing device can then refresh the graphical user interface rendered on the display of the computing device with an updated graphical object—representing the current emotion value—as the selected emotion value is changed by the user.

As the user cycles through the preset range of emotion values, selects an emotion value, or enters an emotion value, the computing device can thus record this new emotion value in Block S120 and visually alter (or "update") the virtual sphere to visually correspond to the current emotion value in Block 130. For example, as the user enters a swipe input into the touchscreen, the computing device can refresh the touchscreen to illustrate the virtual sphere rolling about its spherical center (and about an axis parallel to the lateral axis of the touchscreen) in a direction corresponding to the direction of the swipe input on the touchscreen. Furthermore, in Block S130, the computing device can update the graphical object with an alternate color, geometry, and/or virtual viscosity, etc. in response to a change in the emotion value selection. In one implementation, the computing device renders the virtual sphere in a warmer color and in an increasingly amorphous form in response to selection of emotion values corresponding to increasingly content states of the user (e.g., in response to selections of greater emotion values) in Block S130, and vice versa. In one example, the computing device renders the graphical object: in blue for a current emotion value of "1"; in blue-green for a current emotion value of "2"; in green for a current emotion value of "3"; in yellow-green for a current emotion value of "4"; and in a similar range of colors up to orange for an emotion value of "10." The computing device can also set a virtual viscosity of the sphere that is inversely proportional to the emotion value currently selected. For example, in Block S100, the computing device can render a wax-like virtual sphere that appears relatively rigid for a selected emotion value of "1" but appears more malleable as the selected emotion value increases, such as exhibiting less than 2% deformation of its perimeter from a circle in the plane of the touchscreen for a selected number of 1 but exhibiting up to 20% deformation of its perimeter from the circle for a selected number of 10, and the computing device can update the graphical object rendered on the touchscreen in Block S120 accordingly based on the emotion value currently selected. Therefore, in this example, the virtual sphere can appear as hard wax for a selected emotion value of "1" but appear to warm and soften into a more malleable wax ball as the selected emotion value approaches "10."

However, the computing device can also render a graphical object of any other virtual shape, geometry, color, viscosity, etc., such as a virtual cube, a virtual three-dimensional amoeba, or a graphical avatar. Furthermore, Blocks of the method S100 can be implemented by any other device or system and can collect emotion values from the user in any other way and in any other format.

5. Emotion Value Submission

Block S140 recites recording submission of a final emotion value through the graphical user interface. Generally, in Block S140, the computing device can record a final emotion value selected by the user, store the final emotion value with a time that the emotion value was entered (e.g., in the form of a timestamp) locally on the computing device, and/or upload the emotion value and related metadata (e.g., timestamp, user ID, computing device location) to a remote server or remote database for storage and subsequent handling in Block S150.

In one implementation, the computing device records the current emotion value shown within the graphical user interface (e.g., rendered on the graphical object) in response to a double-tap input over the graphical object, in response to a single-tap input over a "submit" region or other virtual button outside the perimeter of the graphical object rendered on the touchscreen, or in response to any other secondary input into the computing device.

The computing device can also combine metadata with the selected emotion value to generate an emotion package for this emotion value submission, and the computing device can store this emotion package locally, upload the emotion package to a remote server or remote database for remote storage, and/or transmit the emotion package to a computing device associated with a contact or mental health professional affiliated with the user. For example, in Block S140, the computing device can combine the emotion value entered by the user with: the user's username, email address, device ID, or anonymized UUID paired with the user's name or ID in a remote DNS; the last GPS location of the computing device; a time and date of submission of the emotion value (e.g., a "timestamp"); a speed of selection and submission of the emotion value (i.e., the duration of time between a first swipe input over the graphical object and submission of the emotion value); and/or action permissions and/or action triggers (described below) stored locally on the computing device. In this example, the computer system can thus query an integrated geospatial position sensor for the geospatial location of the computing device once an emotion value is submitted by the user and then store this location of the computing device at an approximate time the final emotion value was entered by the user with the selected emotion value in the emotion package.

In Block S140, the computing device can also combine an emotion value selected by the user with a subset of metadata types specific to the selected emotion value to generate the emotion package for the emotion value submission. For example, the computing device can: combine a selected emotion value and a username only into an emotion package for selected emotion values above and including "4"; combine a selected emotion value, a username, a contact trigger (described below), and contact information for a personal contact entered previously by the user for a selected emotion value of "3"; combine a selected emotion value, username, and a therapist trigger (described below) for selected emotion value of "2"; and combine a selected emotion value, a username, an emergency trigger (described below), and a last known GPS location of the computing device for selected emotion value of "1."

The computing device can combine such metadata with an emotion value selected by the user within an alternate lock screen, within a native mental health application, within a native messaging (e.g., email, SMS text message) application executing an alternate keyboard, or within any other interface executing on the computing device, such as described below.

6. Support Group

Figure 5:
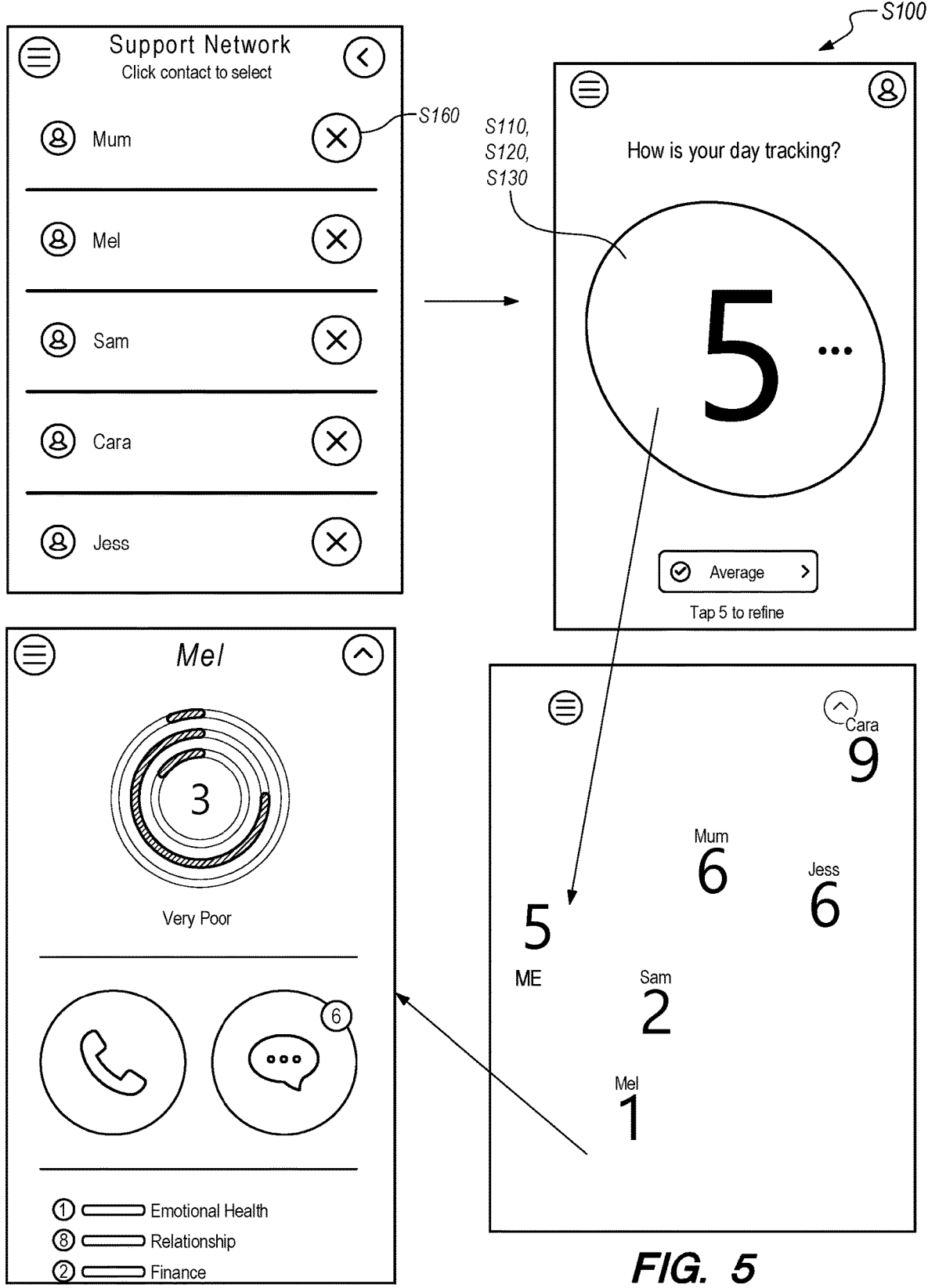
FIG. 5 is a flowchart representation of one variation of the method.

As shown in FIG. 5, one variation of the method S100 includes Block S160, which recites, prior to rendering the graphical object within the graphical user interface, prompting the user to populate a support group with a set of contacts. Generally, in Block S160, the computing device can prompt and/or enable the user to identify one or more friends, family members, mentors, therapists, or other persons who may offer support, guidance, consolation, and/or compassion to the user. The computer system can record names, email addresses, phone number, usernames, account IDs, or other contact information of persons thus selected by the user, populate a support group affiliated with the user with these selected persons, and associate one or more of these members of the user's support group with select triggers implemented in Block S150.

In one implementation in which Blocks of the method S100 are executed locally on the computing device by a native mental health application, the native mental health application accesses a list contacts stored on the computing device, such as in a native contacts application, and prompts the user to select a subset of (e.g., up to five) contacts from the contacts list to form a support group for the user. The native mental health application can then retrieve names, phone numbers, email addresses, and/or other contact information for these selected contacts from the contacts list. Similarly, the native mental health application can prompt the user to select one or more contacts from a list of the user's friends or acquaintances enumerated within an online social network, such as by accessing this list of friends or acquaintances through a native social networking application executing on the computing device; the native mental health application can then implement similar methods and techniques to populate the user's support group with relevant contact information. In another implementation in which the native mental health application functions as a user portal into an emotion tracking and support platform hosting many users, the native mental health application can prompt the user to select one or more other users also on the emotion tracking and support platform. The native mental health application can thus link the user's account to accounts of other users on the emotion tracking and support platform to define a support group for the user. In this foregoing implementation, the native mental health application (or a remote computer system or remote server hosting the native mental health application) can communicate a prompt to each contact selected by the user—such as through a text message, email, communication with the online social network, or in-application notification—to confirm that the contact agrees to support the user.

The native mental health application (and/or the emotion tracking and support platform) can therefore enable the user to select one or more contacts to offer support to the user and to confirm that these contacts agree to join the user's support group. The native mental health application can also prompt the user to join a support network for one or more contacts in her support group or to join a support group for one other person on the emotion tracking and support platform for each contact the user adds to her support group in order to maintain a target or minimum ratio of supporting and supported users on the emotion tracking and support platform.

As shown in FIG. 5, the native mental health application can also gate (i.e., restrict) the user's access to an emotion value submitted by a contact for whom the user has joined a support group until the user enters her own emotion value. In particular, the native mental health application (or the emotion tracking and support platform) can: revealing a second emotion value—previously submitted by a contact of the user through a second instance of the native mental health application executing on a second computing device—to the user at the user's computing device in response to receipt of an emotion value from the user. For example, the native mental health application can: generate a support group of five friends, family members, and/or mentors of the user; incorporate the user into the support group of each of these contacts; and only present recent emotion values of these other contacts to the user once the user has entered her own emotion value. In this example, the native mental health application can require that the user enter at least one emotion value per twenty-four-hour period in order to see all emotion values entered by these related contacts within the same period of time. Therefore, in order to access information needed to support another contact, the user must supply her own emotion value to members of her support group, thereby enabling these other members of the user's support group to access information needed to support the user.

The native mental health application can thus execute on the user's computing device: to populate and maintain a support group for the user; to enable the user to modify account settings and to adjust her support group over time; to control privacy settings; etc. The computing device can also execute Blocks S110, S120, S130, etc. through the native mental health application or through separate applications, such as within an alternate keyboard accessed in a native email, text messaging, or other application or through a lock screen on the computing device, as described below.

The computing device can then distribute prompts to monitor, contact, or show support for the user in Block S150, such as by distributing an emotion value to one or more members of the user's support group, regardless of recipients selected by the user, when the emotion value equals "2" or "3" as described below.

7. Categories

Figure 4:
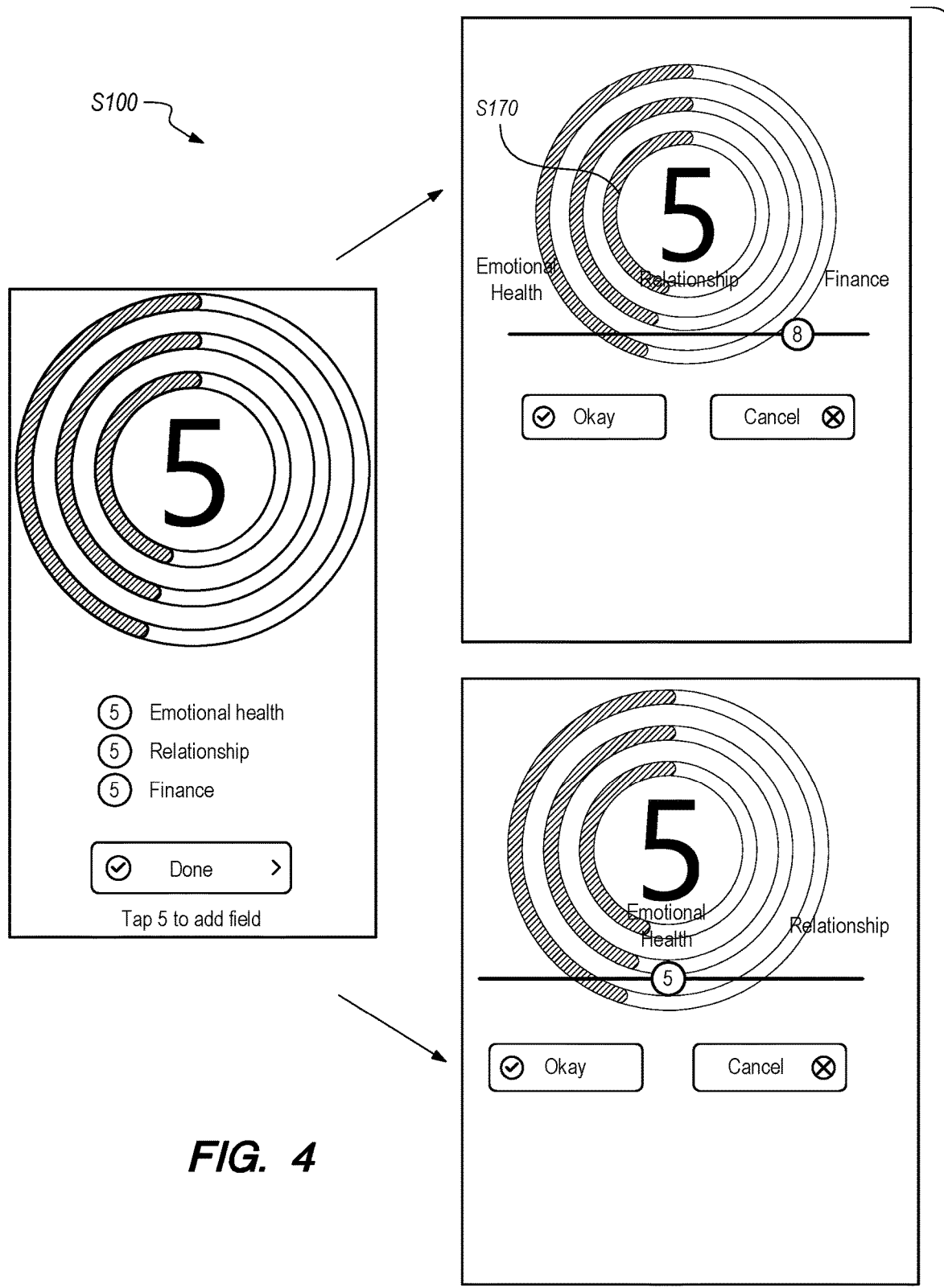
FIG. 4 is a flowchart representation of one variation of the method.
Figure 10:
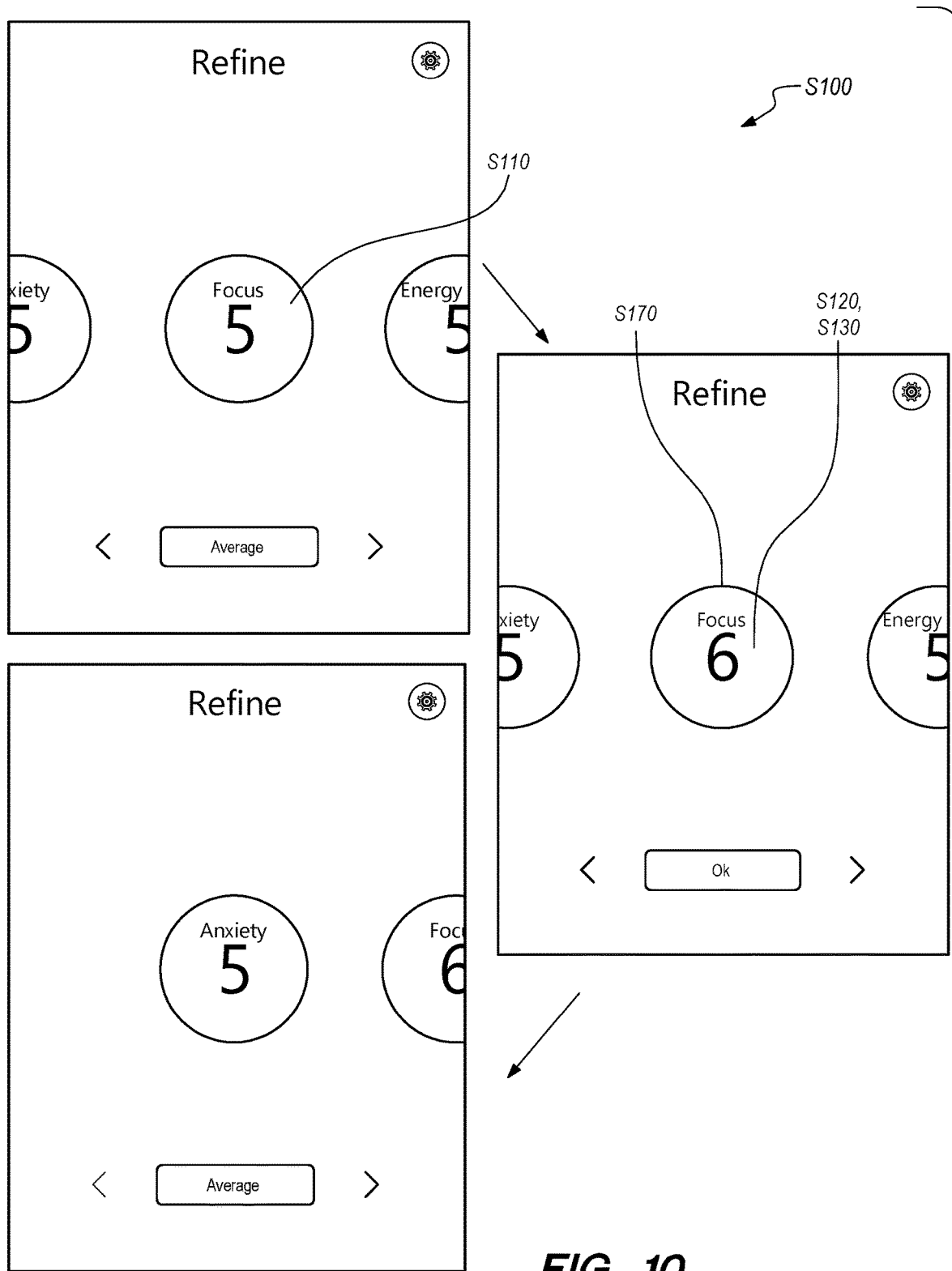
FIG. 10 is a graphical representation of one variation of the method.

As shown in FIGS. 4 and 10, one variation of the method S100 includes Block S170, which recites: receiving a first category label for the final emotion value and storing the final emotion value with the first category label; and recording submission of a second emotion value through the graphical user interface, receiving a second category label different from the first category label for the second emotion value, and storing the second emotion value with the second category label. Generally, in this variation, the computing device can associate an emotion value entered by the user with a specific emotion category and thus automatically determine the context of each emotion value and/or enable members of the user's support group to manually determine the context of the user's emotion value.

Figures 3A, 3B:
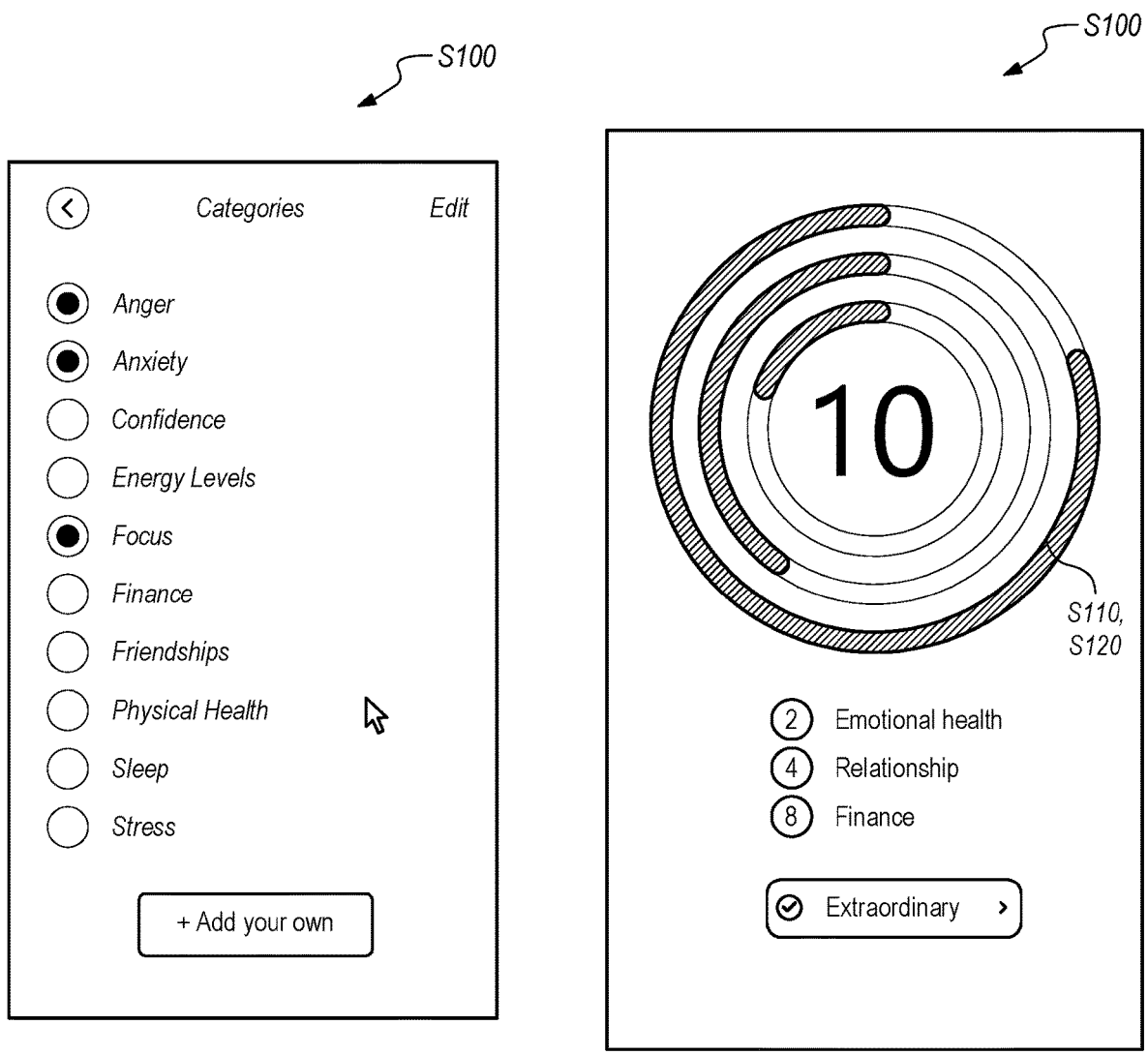
FIGS. 3A and 3B are graphical representations of one variation of the method.

In one implementation, the computing device defaults to labeling the graphical object—representing a current emotion value—with an "overall emotional state" category label and writes an "overall emotional state" label to an emotion value entered by the user when the overall emotional state is current. In this implementation, the computing device can also enable the user to select an alternative category label, such as from a drop down menu, by swiping through a sequence of preset category labels, or by typing a custom category label into a text field. For example, the computing device can enable the user to select one of perceived financial stability, perceived relationship comfort, perceived sleep quality, perceived anxiety level, perceived anger level, perceived physical health, perceived level of confidence, perceived energy level, and/or perceived stress level, etc. of the user before submitting an emotion value, as shown in FIG. 3A. The computing device can then write this label to metadata stored with the emotion value. Immediately upon receipt of a first labeled (i.e., categorized) emotion value at a later time, the computing device can enable the user to enter a second emotion value and to select the same or other label for the second emotion value. For example, within one use episode, the computing device can record: a first emotion value with a first category label corresponding to an overall emotional state of the user; and a second emotion value with a second category label for the second emotion value corresponding to perceived financial stability.

In the foregoing variation in which the computing device populates and maintains a support group for the user, the computing device can link a unique support group to each category selected by the user. The computing device can also implement different trigger values to trigger transmission of a prompt to a member of a support group for each category label. For example, when the user enters an emotion value of "2" or "3" with an "overall emotional state" category label, the computing device can transmit the user's ID, the emotion value, and/or a prompt to contact the user to each member of the user's primary support group in Block S150; in this example, when the user enters an emotion value of "1" or "2" with a "financial security" category label, the computing device can transmit the user's ID (e.g., name), the emotion value, the category label, and/or a prompt—to contact the user—to the user's financial advisor noted in a second finance support group. Therefore, the computing device can: prompt a member of a first support group affiliated with the user and associated with a first category label to contact the user in response to an emotion value equaling the trigger value for the first category label; and prompt a member of a second support group affiliated with the user and associated with a second category label to contact the user in response to an emotion value equaling the trigger value for the second category label.

Alternatively, the computing device can selectively distribute a prompt to contact the user to members of the user's support group based on the emotion value, the corresponding category label, and an expertise noted for each member of the user's support group. For example, when the user enters an emotion value of "2" with an "overall emotional state" category label, the computing device can transmit the user's ID, the emotion value, and/or a prompt to support the user to each member of the user's primary support group in Block S150; in this example, when the user enters an emotion value of "2" with a "financial security" category label, the computing device can transmit the user's ID, the emotion value, the category label, and/or a prompt—to contact the user—to the user's parents noted in the user's support group; and, when the user enters an emotion value of "2" with a "friendships" category label, the computing device can transmit the user's ID, the emotion value, the category label, and/or a prompt to contact the user to the persons—noted in the user's support group—of approximately the same age as the user but not related to the user. The computing device can thus prioritize transmission of prompts—to contact the user—to select members of the user's support group in response to receipt of an emotion value based on each member's known (e.g., user- or member-entered) expertise and the category label assigned to the emotion value.

6. Action Triggers

Block S150 of the method S100 recites, in response to the final emotion value equaling a trigger value, distributing a prompt—to monitor or contact the user—to an external entity. Generally, in Block S150, the computing device (or a remote computer system in cooperation with the computing device) selectively communicates a prompt to an external entity to contact the user—such as immediately or within some time window via textual communication (e.g., SMS text message), in a phone or video conferencing call, or in person—upon receipt of a user-entered emotion value indicating that the user may benefit from immediate support, as shown in FIGS. 1 and 6.

In one implementation, the computing device (or the native mental health application, the emotion tracking and support platform, etc.) distributes prompts to support the user to external entities only when an emotion value equals a trigger value indicating that the user is experiencing relatively low contentment, relatively high anxiety, and/or relatively high concern such that persons possibly in positions to support the user are notified of the user's emotional state only when the user is in greatest need. For example, the computing device can: communicate a first prompt to monitor the user to a computing device associated with a therapist, psychologist, or other mental health professional affiliated with the user upon receipt of an emotion value equaling a first trigger value of "1" from the user; push a notification to interact with the user to a computing device associated with a known contact of the user (e.g., all or a subset of members of the user's support group) in response to the final emotion value equaling a second trigger value of "2" or "3"; and withhold communication of emotion values to persons other than those explicitly selected by the user to receive the user's emotion value (e.g., a recipient of a private text message selected by the user, as described below) for emotion values greater than "3," exclusive.

In Block S150, the computing device (or the native mental health application, the emotion tracking and support platform) can therefore: distribute a dynamic visual object—representing the graphical object in a color value and a virtual viscosity corresponding to an emotion value selected by the user—to a first recipient elected by the user, such as when the user elects to send an emotion value to the user through a native text messaging application or through a native social networking application executing on the computing device as described below; prompt a second recipient (e.g., a member of the user's support group) to contact the user when the emotion value entered by the user equals a first trigger value (e.g., "2" or "3"); and distributes the emotion value to a mental health entity (e.g., a therapist, a psychologist, an emergency responder) when the final emotion value equals a second trigger value (e.g., "1") representing a less content state of the user than the first trigger value.

In another implementation, the native mental health application, lock screen, or alternate keyboard, etc., executing Blocks of the method S100 on the computing device can communicate a static prompt to the user, such as "How are you?"; the user can thus submit an emotion value corresponding to her general feeling or mood. Alternatively, the computing device can communicate one or more distinct prompts to the user at any one time. For example, the computing device can cycle through a prepopulated set of prompts directed toward the user's current feeling or mood about a particular life area, such as a first prompt for general feeling, a second prompt for emotional health, a third prompt for relationship condition, and/or a fourth prompt for financial condition. In this example, the computing device can represent responses to each prompt with a discrete graphical object (e.g., a virtual sphere) specific to the prompt, wherein the graphical object is numbered and colored according to the emotion value selected by the user. The computing device can render these discrete graphical objects together or independently across a set of slides. Alternatively, the computing device can render one graphical object representing a response to the first prompt related to the user's general feeling or mood, and the computing device can render a second graphical object representing responses to emotional health-, relationship-, and finance-related prompts, as shown in FIG. 3B. In Block S140, the computing device can therefore combine the selected emotion value with a pointer to a corresponding prompt or prompt type issued to the user prior to submission of the emotion value, as shown in FIG. 1.

In a similar example, for a prompt relating to the user's general mood or feeling, the computing device (or remote computer system) can dispatch the police and an ambulance to the user's last recorded GPS location in response to submission of an emotion value of "1." In particular, the computing device (or the native mental health application, the emotion tracking and support platform) can dispatch an emergency responder to a last geospatial location of the user's device—extracted from emotion value metadata, as described above—in response to the most recent emotion value entered by the user equaling a trigger value corresponding to a low state of contentment, such as an emotion value of "1" indicating a lowest level of contentment, a highest anxiety, or a greatest level of stress. In this example, in response to a submitted emotion value of "2," the computing device can also transmit a notification to the user's personal or company therapist to call the user or automatically access a calendar on the user's computing device, compare the user's calendar to the therapist's calendar, automatically schedule a call or in-person meeting as soon as possible based on availability of the user and the therapist (or move less important meetings off of the therapist's calendar in order to see the user), and then notify the user and/or the therapist of the scheduled meeting time. Furthermore, in this example, the computing device can push a textual notification to one contact in a preset shortlist of contacts (i.e., members of the user's support group) previously entered by the user in response to a submitted emotion value of "3." In this example, the computing device can cycle through a shortlist of contacts previously entered by the user, such as entered by the user upon installation and first login into a standalone native mental health application, an alternate mental health keyboard, an alternate lock screen application, etc. to populate a personal contacts shortlist, including a phone number and email address for each of a parent, a sibling, a spouse, a best friend, and a mentor. However, in this example, the computing device can execute no action in response to a submitted emotion value of "4" or greater other than to store the submitted emotion value in a local or remote database of emotion values entered by the user and/or to send the emotion value to a contact explicitly selected by the user to receive the emotion value.

In another example, the computing device can: serve a prompt to the user to indicate the user's feeling regarding her finances; transmit a trigger to the user's bank and credit institutions to reject all transactions over $20 if the user submits an emotion value of "1" in response to a finance-related prompt; and access the user's calendar and automatically schedule a call or a meeting with a financial planner if the user submits an emotion value of "2" or less in response to this prompt.

The computing device (or the native mental health application, the emotion tracking and support platform) can implement the foregoing methods and techniques in Block S150 based on a category selected by the user when entering an emotion value (i.e., rather than based on textual or audio prompt served by the computing device to the user over time), as described above.

In Block S150, the computing device can implement standard action trigger and emotion value pairs across a population of users. Alternatively, the computing device can match standard action triggers (e.g., notify a therapist, notify support group members) to select emotion values based on trends or frequencies in emotion values entered by the particular user. For example, the computing device can "normalize" emotion values assigned to action triggers for a particular user based on historical emotion values entered by the user, such as by shifting an action trigger relative to the spectrum of possible quantitative emotion values based on a recent trend in emotion values submitted by the user or based on an average emotion value submitted by the user over an extended period of time (e.g., six months). The computing device can also maintain custom action triggers and corresponding emotion values specific to the user (or to a subset of users within a population), such as triggers to notify a therapist for users who have currently engaged therapists and triggers to notify a best friend for users who have not currently engaged therapists.

Therefore, in the foregoing implementation, the computing device can assign trigger values to emotion values entered by the user based on historical user emotion value data. For example, the computing device can quantify an emotional stability of the user based on a current emotion value and emotion values previously entered by the user based on a magnitude of total deviation from an average emotion value entered by the user over a period of time. In this example, if the user regularly enters emotion values between "1" and "10" with similar frequency, the computing device can label the user as unstable and set a trigger value to connect the user with others at "5" in order to "catch" or slow the user's transition to emotion values of "1." If the user regularly enters emotion values between "3" and "7," the computing device can label the user as moderately stable and set a trigger value to connect the user with others at "3" in order to prompt support of the user when the user is most in need. Furthermore, if the user regularly enters emotion values between "6" and "9," the computing device can label the user as highly stable and set a trigger value to connect the user with others at "4" in order to prompt support of the user when the user's emotional state is declining outside of a regular bound. However, the computing device can characterize the user's emotional stability according to any other schema or schedule and can implement this characterization in any other way to set trigger values for the user.

The computing device can also implement a mental health history of the user to assign triggers to emotion values entered by the user. For example, for a user with a history of self-harm, the computing device can: prompt members of the user's support group to offer support to the user in response to entry of an emotion value of "3" or "4"; prompt a mental health professional to monitor the user in response to an emotion value of "1" or "2"; and dispatch an emergency responder to the user's last known location if the user does not check in with another person or with the user's therapist within one hour of entering an emotion value of "1." However, for a user with a history of harm to others, the computing device can: prompt a mental health professional to monitor the user in response to an emotion value of "1," "2," or "3"; dispatch an emergency responder to the user's last known location if the user does not check in with another person or with the user's therapist within one hour of entering an emotion value of "2"; and immediately dispatch an emergency responder to the user's last known location in response to entry of an emotion value of "1." Furthermore, for a user with no known history of self-harm or harm to others, the computing device can: prompt a mental health professional to contact the user in response to an emotion value of "1"; and prompt members of the user's support group to contact or otherwise support the user in response to entry of an emotion value of "2" or "3."

The computing device (or the native mental health application, the emotion tracking and support platform) can automatically assign such trigger values to emotion values for a user, such as based on digital medical records of the user. Alternatively, the user, a mental health professional, an employer, members of the user's support group, or any other entity can manually assign these triggers to emotion values for the user (or for a population of users).

The computing device (or the native mental health application, the emotion tracking and support platform) can also implement dynamic trigger values. In particular, rather than notifying a member of the user's support group when the user enters an emotion value of "2," the computing device can prompt the support group member to contact the user when the user's entered emotion values are trending downward and take a rapid decline. For example, if the user enters a sequence of emotion values from "9" to "8," then "7, and "then "6," over a period of several hours or two days, the computing device can prompt members of the user's support group to contact the user when the user subsequently enters an emotion value of "5." Similarly, if the user regularly enters emotion values of "8," "9," and "10" but now enters a "4," the computing device can notify members of the user's support group to contact the user to support the user following this rapid decline in the user's emotional state.

7. Prompts

In Block S150, the computing device can serve a variety of prompts to external entities. In one implementation in which the user enters an emotion value equaling a trigger value for contacting an emergency responder, the computing device (or the native mental health application, the emotion tracking and support platform) can transmit an electronic textual notification—including the user's name, location, and concern (e.g., for self-harm or harm to others) from emotion value metadata—to the emergency responder. Alternatively, the computing device can: place an automated call to the emergency responder; or transmit an electronic notification to a mental health professional with metadata for the low emotion value and a prompt to alert an emergency responder. However, the computing device can notify an emergency responder in any other way in Block S150.

In another implementation in which the user enters an emotion value equaling a trigger value for contacting a mental health professional (or other professional service provider), the computing device (or the native mental health application, the emotion tracking and support platform) can transmit an electronic textual notification—such as in the form of a text message, email, or in-application notification—to the mental health professional in Block S150. For example, if the user has an existing relationship with the mental health professional—such as for therapy, psychological testing, or pain management, etc. or if the mental health professional is affiliated with an employer or other organization employing the user—the computing device can generate a textual communication including the user's name, the user's recent emotion value, the user's location, the user's contact information (e.g., phone number), and/or a prompt to call, message, or otherwise monitor the user. In particular, in Block S150, the computing device can prompt a mental health professional to contact the user directly or to monitor the user, such as by tracking the location of the user's computing device through a web-based doctor portal or by contacting persons physically near the user or family or friends of the user. However, if the user is not currently affiliated with a mental health professional, the computing device can issue a notification to the user to confirm that the user would like to connect to a mental health professional, and the computing device can automatically select a mental health professional from a directory and connect the user to the mental health professional, such as via text, email, or phone call, in Block S150 following confirmation from the user. However, the computer system can prompt a mental health professional to contact or monitor the user in any other way in Block S150 in response to entry of a emotion value equaling a corresponding trigger value.

In another implementation in which the user enters an emotion value equaling a trigger value for contacting a peer or a member of a support group, the computing device (or the native mental health application, the emotion tracking and support platform) can push a notification to show concern for the user to such a recipient. For example and as described above, the computing device can push an electronic notification—such as a text message, email, or in-application notification to call or message the user—a member of the user's support group, regardless of the recipient of the emotion value elected by the user, in response to entry of an emotion value of "2" or "3." In this example, the computing device can generate a notification including the user's phone number, the user's email address, a link to a messaging center in which the recipient can message the user, etc., and the recipient can use this contact information to contact the user.

The computing device can additionally or alternatively generate such a notification that includes prompts to the recipient to show care or concern for the user in other ways.

For example, the computing device can generate a notification that recites, "Jess is feeling down. Send her a song that has special meaning to your relationship with her." In this example, the computing device can incorporate a link (e.g., a website URL, an in-application link) to a digital music service (e.g., a commercial music streaming service) into the notification; upon selection of the link, the recipient can access the digital music service, navigate to a particular song, and select this song to share with the user; the emotion tracking and support platform or other messaging service can load a link to this song into a new communication from the recipient to the user and transmit this new communication to the user; upon receipt of this new communication at the computing device, the user can select this link, and the computing device can stream the song from the digital music service. The computing device can thus prompt and enable a contact of the user (e.g., a member of the user's support group) to send the user a song that may have special meaning to the user rather than calling or text messaging the user. However, in this example, the computing device (or the native mental health application, the emotion tracking and support platform) can interface with a music streaming service in any other way to replay a song selected by the user's contact for the user.

In another example, the computing device can generate a notification that recites, "Jess is feeling down. Send her an old photo of the two of you doing something you really enjoyed," and the computing device can send this notification to a recipient upon entry of a low emotion value by the user. In this example, the emotion tracking and support platform can then communicate a digital photograph—selected by the recipient at the recipient's computing device (e.g., smartphone)—back to the user's computing device, and the user's computing device can render the digital photograph within a notification or within the native mental health application executing on the user's computing device. The computing device can similarly prompt the recipient to send a video, digital sketch, or other media to the user in response to entry of a low emotion value by the user. However, the computing device (or the native mental health application, the emotion tracking and support platform) can prompt a recipient to send any other media to the user and can present such media to the user in any other way.

In another example, the computing device can generate a notification that includes a prompt to physically visit the user and can send this notification to a particular recipient, such as a recipient physically near the user. In this example, if the user enters a low emotion value into her computing device, the computing device can: query an internal GPS sensor for the user's current location; cross reference the user's location to locations of members of the user's support group to prioritize members of the support group by proximity to the user (e.g., by building, street, campus, city, region, state); and select a member of the support group nearest the user to receive this notification.

In yet another example, the computing device can generate a notification that includes a prompt to send the user a physical gift. In this example, the computing device can include the user's current location or address, a link to an online florist, and a prompt to send flowers to the user in a notification sent to the recipient; upon receipt of the notification, the recipient can select the link to access the online florist, select a flower arrangement, and submit payment and delivery details in order to initiate delivery of flowers to the user. Similarly, the computing device can prompt the recipient to send a pair of socks, a meal, a coffee, or other tangible good to the user in response to entry of a low emotion value by the user, such as by incorporating links to online retailers through which the recipient may select and purchase a good for delivery to the user.

In another example, if the user enters a low emotion value equaling a trigger value for involvement of a therapist or other mental health professional, the computing device (or the native mental health application, the emotion tracking and support platform) can also generate a notification to subsidize a session with the mental health professional and then communicate this notification to one or more members of the user's support group. In particular, the computing device (or the native mental health application, the emotion tracking and support platform) can prompt members of the user's support group to supply all or partial payment for the user to complete a session with a therapist or other mental health professional, such as if the user enters a low emotion value (e.g., a "1" or a "2") with an "overall emotional state" category label and enters a similarly low emotion value (e.g., a "1," "2," or "3") with a "financial security" category label. The emotion tracking and support platform can thus collect funds from these recipients and release these funds to the user or to a selected therapist following completion of a session. Alternatively, recipients of such a prompt can transfer funds to the user or to the therapist through other external currency transfer services.

However, the computing device (or the native mental health application, the emotion tracking and support platform) can generate and transmit a notification including a prompt for any other action to a member of the user's support group or other recipient in response to entry by the user of an emotion value equaling a corresponding trigger value. The computing device can also index through these notification types over time. The computing device can also selectively issue these various notification types to recipients based on: one or more category labels entered by the user; proximity of recipients to the user; perceived financial security of recipients (e.g., by sending a prompt to send funds or to send a physical gift only to recipients with current emotion values with "financial security" category labels exceeding "5"); a familial or friendship status with the user; an age gap with the user (e.g., by prompting recipients of the same age to send a song but prompting recipients substantially older than the user to call the user); etc.

Therefore, by varying a notification type sent to a recipient in Block S150 in response to a low emotion value entered by the user, the computing device may disguise a consequence of entry of a emotion value from the user. In particular, if the user is not certain that a phone call or text message from a family member or friend will follow entry of a low emotion value but rather that a wider variety of support modes are possible, the user may be more likely to enter honest emotion values over time. Similarly, receipt of flowers, a song, or other digital or physical media following entry of a low emotion value may abstract such a gift or media from the low emotion value, thereby curbing the user's expectations that a gift of other media may follow entry of a low emotion value such that the user may be more likely to enter honest emotion values over time.

8. Lock Screen

Figure 8:
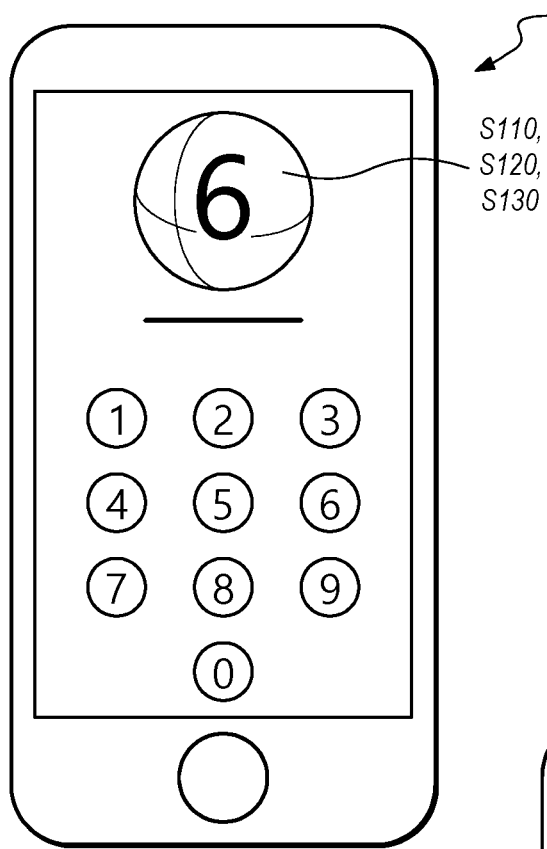
FIG. 8 is a graphical representation of one variation of the method.

In one variation, the computing device executes Blocks of the method S100 S100 within an alternate lock screen, as shown in FIG. 8.

In this variation, in Block S100, the computing device can render the graphical object on the touchscreen in response to an initial input that transitions the computing device out of a standby mode. The user can then swipe up or down on the touchscreen to pull an emotion value—in the range of emotion values—into the graphical object, and the computing device can update the graphical object rendered in the lock screen accordingly in Block S120. The user can continue to swipe over the lock screen to cycle through the range of emotion values until an appropriate emotion value is reached, and the computing device can update the graphical object—including its color, viscosity, and emotion value—in Blocks S120 and S130 according to each additional swipe entered by the user. Once the appropriate emotion value is reached, the user can enter a passcode through an alphanumeric keypad adjacent the graphical object or in an alternate screen of the lock screen to unlock the computing device and enter the emotion value. Alternatively, the user can double tap the graphical object, select an alternate region on the touchscreen, trace a passcode pattern, or enter any other input into a touchscreen of the computing device to unlock the computing device and to submit the selected emotion value. The computing device can then record this emotion value in Block S130, unlock the computing device, and then handle the selected emotion value as described herein.

Therefore, in this variation, the computing device (e.g., a smartphone) can: render a graphical object (e.g., a virtual sphere) within a lock screen, such as adjacent a numeric keypad in Block S100; record an emotion value selected by the user in response to entry of a correct passcode into the lock screen (and store this emotion value in a local or remote database of emotion values entered by the user) in Block S140; and distribute a prompt—to contact the user—to an external entity in response to the emotion value—entered through the lock screen upon receipt of the correct passcode—equaling a trigger value.

In this variation (and in other variations), the computing device can alter the initial emotion value applied to the graphical object with each subsequent unlock cycle (or with each subsequent entry of an emotion value) in order to require the user's active attention when swiping to the appropriate number. In particular, by both pseudorandomly changing the initial emotion value inserted into the graphical object upon each new unlock cycle and automatically executing actions in response to entry of select emotion values (e.g., 1, 2, and 3), the computing device can encourage the user to deliberately and attentively swipe to an appropriate number rather than simply thoughtlessly swiping to an emotion value and selecting a submit key. Similarly, the computing device can change how swipe directions (e.g., up or down) correspond to index directions (e.g., increasing and decreasing) for cycling through the range of emotion values and can modify swipe distances that trigger an index event for cycling through the range of emotion values for each new unlock cycle to achieve similar effects.

Furthermore, in the foregoing and other implementations, the computing device can: pseudorandomly assign an initial emotion value—in a spectrum of emotion values corresponding to unique contentment states of the user—to the graphical object; and index through this spectrum of emotion values in a loop—sequentially or in a pseudorandom order—according to a sequence of inputs into the graphical user interface. In particular, by varying a start value and/or an order through which emotion values in the range or spectrum of emotion values are cycled through responsive to user inputs into the computing device, the computing device can prompt the user to pay greater attention to which emotion value is selected before submitting a final emotion value, which may elicit greater honesty in emotion value submissions by the user. Furthermore, the computing device (or the native mental health application, the emotion tracking and support platform, etc.) can characterize an integrity of an emotion value entered by the user based on a number of swipe (or other) inputs entered by the user into the computing device before reaching a final emotion value. For example, if the number of swipe inputs entered by the user historically falls between no swipe input and two swipe inputs for a pseudorandom order of emotion values but the user's selected emotion values exhibit large swings between "1" to "10," the computing device can characterize the honesty of the user's inputs (or engagement with the native mental health application) as low. However, if the user regularly swipes between one and six times when selecting an emotion value and enters emotion values than exhibit relatively smooth changes over time, the computing device can characterize the honesty of the user's inputs (or engagement with the native mental health application) as high.

8. Keyboard

Figure 7:
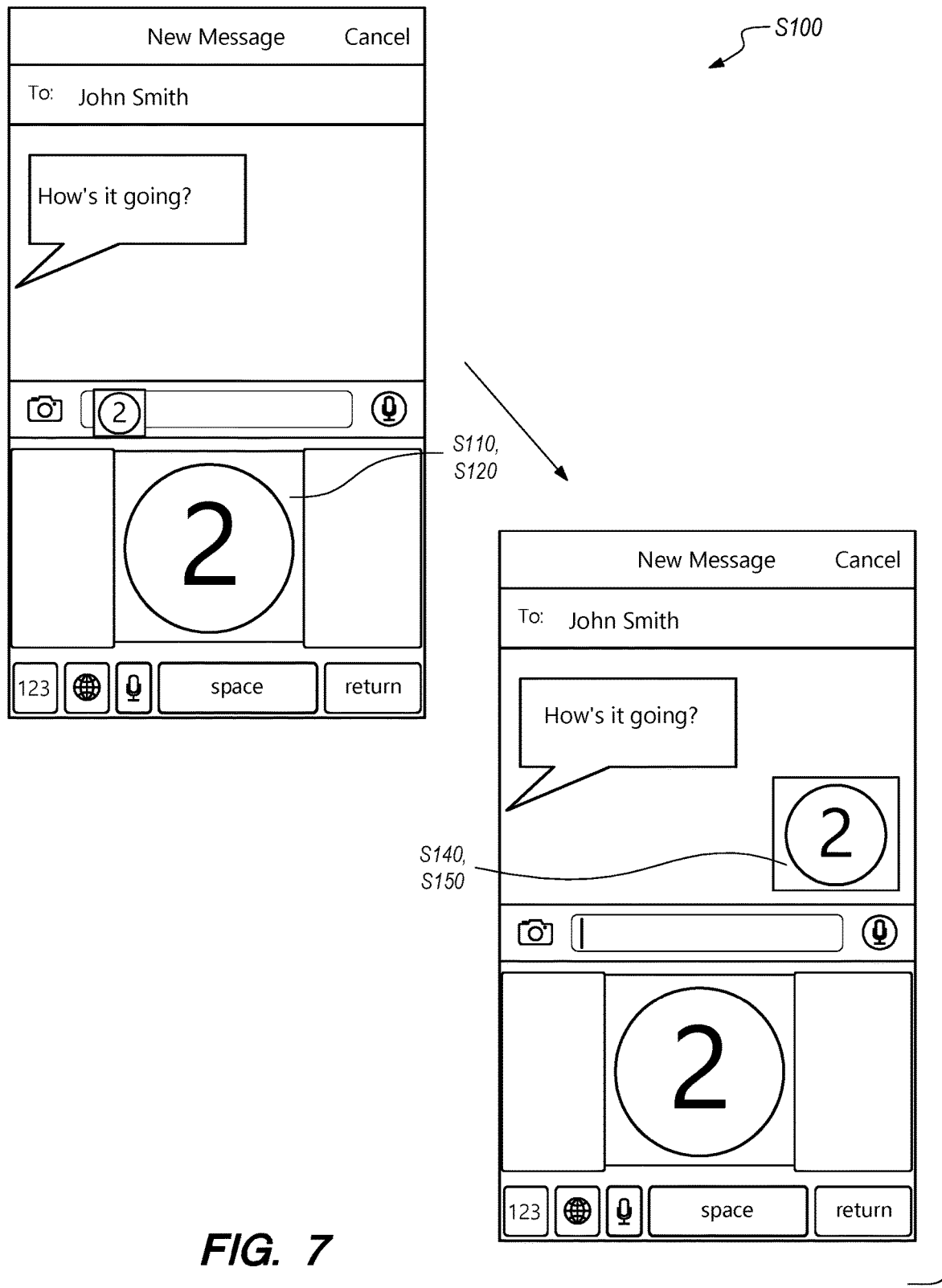
FIG. 7 is a flowchart representation of one variation of the method.

In another variation, the computing device executes Blocks of the method S100 S100 within an alternate keyboard, as shown in FIG. 7. In this variation, in Block S100, the computing device can render the graphical object within a keyboard area as the user drafts or reviews textual content within any one or more native applications executing on the computing device. In particular, rather than discrete keys representing discrete alphanumeric characters, the alternate keyboard includes an instance of the graphical object rendered within a defined keyboard area, and the alternate keyboard updates the emotion value, color, and/or geometry, etc. of the graphical object within the keyboard area in Blocks S120 and S130 in response to swipe gestures entered by the user over the keyboard area, such as described above.

In one example application, while in a native text messaging application executing on a computing device, the user can switch to the alternate keyboard and swipe over the graphical object to select an emotion value, as in Blocks S100 and S120. In response to a double tap input over the graphical object, a selection within the keyboard area and outside of the graphical object, or any other suitable input, the alternate keyboard can load a static image of the graphical object—including the final color, shape, and emotion value of the graphical object—into a message preview within the text messaging application in Block S140, as shown in FIG. 1. The text messaging application can then transmit the image of the graphical object to a selected recipient in response to selection of a virtual "send" button by the user. In this example application, the alternate keyboard can alternatively load a dynamic image, such as a GIF or video file showing the virtual object rotating about its center, deforming according to its assigned viscosity corresponding to the selected emotion value, and/or pulsing within a narrow color band corresponding to selected emotion value, such as described above. Furthermore, in addition to sending the static or dynamic image of the graphical object to the recipient, the alternate keyboard can also generate, store, and/or distribute the selected emotion value and select metadata. For example, the alternate keyboard can store the selected emotion value, the time and date the emotion value was sent to the recipient, and other metadata, as described above, in local memory on the computing device. The alternate keyboard can also encrypt and push these data to a remote database for storage with other user-specific data, or the alternate keyboard can anonymize and push these data to a remote database for storage with other anonymized population data.

In this foregoing example application, the recipient can push to the user—through a similar native text messaging application—a prompt to submit an emotion value corresponding to the user's general mood or feeling, the user's emotional health, the user's relationship condition, or the user's financial condition, and the user can switch to the alternate keyboard, swipe the graphical object to select an appropriate emotion value, and transmit this emotion value back to the recipient.

The recipient's computing device can thus execute a second instance of the alternate keyboard, and the recipient can open this second instance of the alternate keyboard within a text messaging application executing on the recipient's computing device to select from a prepopulated list of prompts to send to the user. For example, the instance of the alternate keyboard executing on the recipient's computing device can include options to send any one or more of the following prompts to the user: "How are you feeling?," "How are things with your spouse?," "How is your emotional health?," and/or "How are things going financially?" Thus, the recipient can select a particular prompt from this prepopulated list of prompts and send this prompt to the user, and the instance of the alternate keyboard executing on the user's computing device can write a flag for a prompt type corresponding to the particular metadata stored with the emotion value submitted in response to the particular prompt. Alternatively, the instance of the alternate keyboard executing on the user's computing device can implement natural language processing techniques to determine a prompt type from one or more messages sent by the recipient to the user—or vice versa—leading up to the time that the user submitted the emotion value to the recipient; the instance of the alternate keyboard executing on the user's computing device can thus add a flag for the corresponding prompt type to metadata associated with the selected emotion value.

In the foregoing example application, the alternate keyboard can also automatically transmit (or trigger transmission of) a prompt to an emergency responder, such as described above, in response to transmission of an emotion value of "1" to the recipient. The alternate keyboard can similarly connect the user with a therapist or to a contact on a preset contact shortlist, such as described above, in response to transmission of an emotion value of "2" and an emotion value of "3," respectively, to the recipient.

The alternate keyboard can implement similar methods and techniques within a native email application executing on the user's computing device. For example, while composing an email within the native email application, the user can select the alternate keyboard, swipe the graphical object to select a relevant emotion value, and then insert a static or dynamic image representing the selected emotion value and the graphical object into an open email draft. The alternate keyboard can store the selected emotion value and related metadata and distribute relevant action triggers, as described above. The alternate keyboard can also scan the body of the user's email, such as including text entered by the user and text in earlier emails in the same email thread—and implement natural language processing techniques to determine the context of (i.e., a prompt type associated with) the selected emotion value, as described above.

The alternate keyboard can thus interface with a native text messaging application and/or a native email application executing on the user's computing device to enable the user to send an emotion value to a recipient while enabling additional emotion value tracking and action trigger handling, as described above. The alternate keyboard can also interface with a native application specific to a health clinic or to an employer to enter emotion values into fields corresponding to physical health-, mental health-, and/or productivity-related prompts. Alternatively, the native messaging application can characterize emotion values typed into the message preview by the user and can implement methods and techniques described herein accordingly.

In this example application, the computing device can access an alternate keyboard containing the graphical object and enabling the user to cycle through emotion values assigned to the graphical object by entering swipe (or other) inputs into the alternative keyboard. Once a final emotion value is selected by the user, the computing device can write the graphical object—including color, virtual viscosity, and/or other parameters corresponding to the final emotion value—to a message or other text field within a textual communication application (e.g., a native email application, a native SMS text messaging application, or a native social networking application, etc.) executing on the computing device and then transmit this message, including the graphical object, to a recipient selected by the user. Upon receipt of the graphical object, such as in a private text message or through a public post in an online social network, the recipient of the graphical object can thus quickly, visually distinguish the user's emotional state based on the color, emotion number, and other parameters represented by the graphical object. In particular, the graphical object can be colored and move according to the user's selected emotion value, as described above. The computing device can share this graphical object with a recipient explicitly selected by the user (e.g., one person in a private text message, the user's social feed in an online social network) when the emotion value exceeds general or user-specific trigger values with the textual communication application executing on the computing device. However, the computing device can share the graphical object and/or emotion value with other entities (e.g., member of the user's support group, the user's therapist) if the entered emotion value equals a trigger value assigned to the user, as described above, such as automatically or following additional confirmation from the user to share the emotion value.

Therefore, the computing device can: access an alternate digital keyboard—in replacement of an alphanumeric keyboard—within a native textual communication application executing on a mobile computing device and render the graphic object within a message preview area of the alternate digital keyboard in Block S100; index the emotion value represented on the graphical object in response to and in a direction corresponding to a swipe input over the message preview area in Block S120; transmitting the graphical object to a recipient selected in the native textual communication application through a private messaging channel in response to receipt of a command at the native textual communication application to send the graphical object to the recipient, such as in the form of a digital file, in Block S150; and withhold the final emotion value from the external entity in response to the final emotion value differing from the trigger value in Block S150. The computing device can also: record a final emotion value selected by the user within the native text messaging application to a database of emotion values entered by the user in Block S140; transmit a form of the final emotion value and an identifier of the user to a mental health representative in response to the final emotion value equaling the trigger value (e.g., "1") in Block S150; and/or communicate a form of the final emotion value to a contact specified in the user's support group and distinct from the original user-elected recipient in response to the final emotion value exceeding the trigger value and a threshold intervention value exceeding the final emotion value (e.g., equal to a second trigger value of "2" or "3"). The computing device can therefore execute Blocks of the method S100 to distribute the user's emotion value from one recipient selected by the user to many recipients suited to support the user in a time of need.

Similarly, the computing device can: access an alternate digital keyboard within a native online social networking application executing on a mobile computing device and render the graphic object within a message preview area of the alternate digital keyboard in Block S100; update a visual form of the graphical object within the preview area to correspond to the emotion value in response to the input into the graphical user interface in Block S120; post the graphical object to a social feed within an online social network in response to receipt of a command at the native online social networking application to post the graphical object to the online social network; and communicate a prompt to a contact affiliated with the user in response to the final emotion value equaling a trigger value, wherein the prompt directs the contact to the social feed or to contact the user directly. The computing device can therefore execute Blocks of the method S100 to distribute the user's emotion value from many recipients to one particular well-suited to support the user in a time of need.

10. Application: Mental Health Clinic

In another variation, Blocks of the method S100 are executed within a native mental health application executing on the user's computing device. In this variation, a mental health clinic, rehabilitation center, hospital, or similar institution can track mental health statuses of in-patient and out-patient populations over time through instances of the native mental health application executing on personal or institution-issued computing devices. Each instance of the native mental health application executing on a computing device affiliated with a user (e.g., a patient) can implement an internal graphical user interface, the alternate keyboard, and/or the alternate lock screen described above.

In this variation, the native mental health application can issue regular prompts—such as general, mental health-, relationship, or finance-related prompts, as described above—to the user to check-in with an emotion value submission, such as every morning, every afternoon, and every evening. Alternatively, the native mental health application can issue such prompts at dynamic intervals. For example, the native mental health application can issue a higher frequency of check-in prompts to the user for lower emotion values last submitted by the user. In this example, the native mental health application can issue prompts to the user at a frequency of every ten minutes for a last emotion value of "1," every 30 minutes for a last emotion value of "2," every hour for a last emotion value of "3," every two hours for a last emotion value of "4," etc. The native mental health application can also issue prompts to the user at frequencies based on whether the user is inpatient or outpatient (e.g., 20% higher check-in prompt frequencies for outpatients than for inpatients) and/or based on trends in emotion values submitted by the user (e.g., a lower frequency of check-in prompts if the user is trending toward higher submitted emotion values).

In this variation, a therapist or mental health specialist can access a dashboard (e.g., within a native mental health management application, within a web browser) to manually issue a check-in prompt to all or a subset of the affiliated patient population. The native mental health application can also automatically connect the user with this therapist, this specialist, an advisor, or an other contact based on an emotion value submitted by the user, as described above.

In this variation, each patient in the patient population can be associated with a particular health condition or set of health conditions, and the native mental health application (or the native mental health management application, the remote computer system, a remote database, etc.) can assign a general prompt, a set of lower-level prompts, and/or a set of action triggers to a particular patient based on the particular patient's current health condition. In one example, for a first user who is an alcoholic, an instance of the native mental health application executing on the first user's smartphone: can connect the first user with a member in the first user's support group in response to submission of an emotion value of "3"; connect the first user with her sponsor in response to submission of an emotion value of "2"; and dispatch the first user's sponsor, a psychotherapist, and/or a police officer to the last known GPS location of the first user's smartphone in response to submission of an emotion value of "1." In this example, for a second user who is clinically depressed and exhibits suicidal tendencies, an instance of the native mental health application executing on the second user's smartphone: can connect the second user with a close friend in response to submission of an emotion value of "3"; connect the second user with her psychiatrist in response to submission of an emotion value of "2"; and dispatch the second user's psychiatrist and an ambulance to the last known GPS location of the second user's smartphone in response to submission of an emotion value of "1" by the second user.

11. Application: Employer

In another variation, Blocks of the method S100 are executed within a native employer application executing on a computing device (e.g., a smartphone, a tablet) affiliated with the user. In this variation, an employer can track mental health statuses of its employees during (and outside of) work hours through instances of the native employer application executing on personal or employer-issued computing devices. Each instance of the native employer application executing on a computing device affiliated with a user (e.g., an employee) can implement an internal graphical user interface, the alternate keyboard, and/or the alternate lock screen described above and as shown in FIG. 9.

In this variation, emotion values entered by an employee in response to a general feeling, mood, anxiety, and/or other mental or physical health-related prompt may remain concealed to the employer. In particular, an instance of the native employer application or a remote computer system cooperating with the instance of the native employer application can anonymize emotion values submitted by employees before communicating these data through an employer portal to track mental health, anxiety, etc. across an employee population, or the native application and/or remote computer system can withhold employee-entered emotion values from representatives of the employer (e.g., managers) and instead automatically distribute these data to select third-party services contracted by the employer. For example, the native employer application and/or the affiliated remote computer system can automatically distribute notifications to emergency personnel in response to emotion values of 1 submitted by employees and automatically distribute employee data and prompts to third-party contracted therapists or psychologists in response to emotion values of 2 submitted by employees, as described above.

In one implementation, the native employer application executing Blocks of the method S100 can also serve productivity-related prompts to users through an internal graphical user interface, through the alternate lock screen, and/or through an alternate keyboard within a native messaging application. In this implementation, the native employer application can communicate emotion values entered by employees in response to productivity-related prompts to an employer representative, such as to an human resources representative or to the user's manager to track the user's feelings about productivity during work hours. For example, an instance of the native employer application or a remote computer system hosting the native employer application can automatically identify trends in an employee's feeling about her productivity and submit related suggestions to a representative of the employer (e.g., a manager) accordingly. For example, as an employee enters emotion values in response to productivity-related prompts over time, the remote computer system can aggregate and process these emotion values to determine that the user tends to feel most productive between the hours of 8 AM and 1 PM (e.g., a time window corresponding to high frequencies of emotion values above 6), tends to feel much less productive between the hours of 1 PM and 3 PM (e.g., a time window corresponding to high frequencies of emotion values below 5), and tends to regain productivity between 3 PM and 5 PM on weekdays. To preserve employee work satisfaction, the remote computer system can issue a suggestion to the employee's manager to implement a break period from 1 PM to 2 PM for the employee during a one-week trial period. In this example, the remote computer system can continue to receive and track emotion values entered by the employee in response to productivity-related prompts issued during work hours; if the employee shows increased productivity in the hour from 2 PM to 3 PM, the remote computer system can transmit a suggestion to the employee's manager to extend the trial period or to make the break period mandatory for the user.

In one example application, an airline issues a native employer application to its grounds crews, pilots, and/or stewards to collect regular check-ins from its employees during operating hours. In one example, an instance of the native employer application executing on a smartphone issued to a pilot, the native employer application can prompt the pilot to check-in before a flight assigned to the pilot, such as: 1 day before, 12 hours before, 8 hours before, 4 hours before, 2 hours before, 1 hour before, 30 minutes before, and 5 minutes before doors are closed to initiate the flight. In this example, the airline can automatically ground the pilot if he enters an emotion value of "1" or "2" within three days of the departure of an assigned flight, and the airline can automatically ground the pilot if he enters more than three emotion values of "3" within 24 hours of the scheduled departure of a flight assigned to the pilot. Furthermore, in this example application, the native employer application can prompt the pilot to check-in during the flight, such as every hour throughout the flight. The native employer application can also increase a check-in frequency during a flight, such as once at the first hour, again at the fourth hour, at the eight hour, at the tenth hour, at the twelfth hour, at the thirteenth hour, at the fourteenth hour, etc. during the flight. The native employer application can interface with a remote computer system (e.g., a remote server) and computing devices issued to a second pilot and stewards on the plane with the pilot to issue prompts related to the emotion values submitted by the pilot. For example, if the instance of the native employer application executing on the pilot's smartphone transmits an emotion value of "2" or less to an affiliated remote server during the flight, the remote server can broadcast notifications to smartphones affiliated with the second pilot and onboard stewards to remove the pilot from the cockpit.

In the foregoing example application, an instance of the native employer application can execute on a tablet issued to a grounds crewman to collect emotion values from the grounds crewman through an alternate lock screen, as described above. For example, the native employer application can require the grounds crewman to unlock the tablet by entering an emotion value in response to a prompt of one or more types, as described above, in order to access a digital pre-flight checklist for the aircraft or a refueling checklist, as shown in FIG. 9. Alternatively, the employer can require the grounds crewman to open the native employer application and enter an emotion value at select times during work hours or before performing certain tasks, such as before opening bay doors on an aircraft to load or unload luggage. In another example, the native employer application can execute on a digital control panel mounted on or near a cockpit door of an aircraft and can execute Blocks of the method S100 S100 to prompt a pilot (or steward) to enter an emotion value into the digital control panel before unlocking the cockpit door.

Therefore, in this example application, the computing device can execute Blocks of the method S100 to gate access to content on the computing device (e.g., an application executing on the computing device) until an emotion value is selected and submitted by the user. For example, the computing device—issued to the user—can: restrict access to an employer-issued checklist until the final emotion value is selected by the user and submitted through the graphical user interface; and then communicate the emotion value entered by the user and an identifier of the user to a mental health professional or other entity affiliated with the employer in response to the entered emotion value equaling a trigger value.

In another example application, a mining operation contracts a mental health application that prompts miners employed by the mining operation to submit emotion values in response to mental health-related prompts when punching in, when punching out, at the beginning of each shift, and/or at the beginning of each break period, such as through a digital punch clock arranged at an entrance of a mining facility or through computing devices issued to each miner or miner group within the mining operation. In this example implementation, the mental health application and/or an associated remote computer system can automatically discharge a therapist—employed by the mining operation or contracted by the operation—to a particular miner or automatically instruct the particular miner to visit an onsite therapist if the particular miner enters an emotion value of "1" or "2," such as described above.

In this variation, Blocks of the method S100 can be executed by equipment rather than by discrete computing devices (e.g., a smartphone, a tablet, a smart watch) assigned to particular employees. For example, when an employee swipes a badge, enters a fingerprint, or logs into a machine with an username and password within an employer's facility, an interlock on the machine can execute Blocks of the method S100 to present the user with a prompt to enter an emotion value corresponding to the user's current mood, feeling, confidence, or productivity, etc., such as by swiping a rendered graphical object or by typing an emotion value on a touch screen within the interlock, as described above. The interlock can then grant access to the user upon receipt of an emotion value thus entered. In this example, the interlock can associate the submitted emotion value with an employee ID, name, or other identifier of the user to generate an emotion package, as described above and then push this emotion package to a remote computer system; the computer system can then implement methods and techniques described above to selectively connect the employee with a preselected contact, a therapist, or an emergency responder based on general or custom action triggers, as described herein.

11. School

In another variation, Blocks of the method S100 are executed within a native student application executing on a computing device assigned to or accessed by a student. For example, an elementary school, middle school, or high school can issue mobile computing devices executing Blocks of the method S100 to students in order to track mental health statuses of its students during (and outside of) school hours. In this example, each instance of the native student application can implement methods and techniques described above to collect emotion values entered by a corresponding student in response to one or more prompts, such as in response to check-in prompts issued during certain times of the day (e.g., at the beginning of a school day and following a lunch break) or at the start of each class. Each instance of the native student application can thus respond to action triggers, as described above, by connecting a student to a counselor, advisor, or teacher based on select emotion values entered by the student. Each instance of the native student application can also collect student-entered emotion values into a journal for select distribution to parents and/or teachers affiliated with the school.

11. Guns

In another example, the native mental health application is executed by an electronic gun case, an electronic gun lock installed on a gun, or a smartphone or other mobile device wirelessly paired to the electronic gun case or electronic gun lock. In this example, the native mental health application can prompt a user to enter an emotion value before unlocking the electronic gun case or electronic gun lock and can implement methods and techniques described above to notify a member of a support group, a therapist, or an emergency responder (e.g., policy, a security agency, etc.) if the user enters corresponding emotion values, such as "3," "2," or "1," respectively before retrieving or unlocking a gun.

In a similar example, Blocks of the method S100 can be executed by a native gun ownership application executing on a smartphone. In this example, the native gun ownership application can implement methods and techniques described above to regularly (e.g., daily) prompt a gun owner to enter an emotion value. Upon receipt of a substantially low emotion value, such as "1" or "2," the native gun ownership application can communicate the location of the smartphone—and therefore the location of the gun owner—and a warning to an emergency responder (e.g., a police department, a security agency) and/or to other people near the gun owner, such as the gun owner's family members, friends, neighbors, coworkers, etc.

12. Network Access

In another example, the native mental health application—executing on a computing device—executes Blocks of the method S100 to prompt a user to enter an emotion value when the computing device attempts to connect to a wireless network, such as a cellular network or a Wi-Fi hub within a hospital, airport terminal, or military base. The computing device can return an emotion value entered by the user to the wireless network in order to gain access to the wireless network, and a remote computer system can execute other Blocks of the method S100 to respond to the user's emotion value, as described above.

However, Blocks of the method S100 can be executed in any other employment, teaching, or operations environment to collect and track feedback pertaining to mental health, physical health, satisfaction, and/or productivity, etc. from one or more employees or affiliates.

The systems and methods of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

I claim:

1. A method for tracking and responding to mental health changes in a user, the method comprising:
   at a first time:
      rendering a first graphical object within a graphical user interface;
      pseudo-randomly assigning a first emotion value, in a spectrum of emotion values corresponding to unique contentment states of the user, to the first graphical object;
      indexing the first emotion value assigned to the first graphical object through a spectrum of emotion values according to a direction of an input into the graphical user interface;
      within the graphical user interface, updating the first graphical object to visually correspond to the first emotion value assigned to the first graphical object;
      characterizing a first integrity of a first final emotion value based on a first quantity of inputs over the first graphical object preceding selection of the first final emotion value;
      in response to the first integrity exceeding a threshold integrity, recording submission of the first final emotion value through the graphical user interface; and
      in response to the first final emotion value equaling a first trigger value, distributing a prompt to an external entity to monitor the user; and
   at a second time:
      rendering a second graphical object within the graphical user interface;
      pseudo-randomly assigning a second emotion value, in a spectrum of emotion values corresponding to unique contentment states of the user, to the second graphical object;
      indexing the second emotion value assigned to the second graphical object through a spectrum of emotion values according to a direction of an input into the graphical user interface;
      within the graphical user interface, updating the second graphical object to visually correspond to the second emotion value assigned to the second graphical object;
      characterizing a second integrity of a second final emotion value based on a second quantity of inputs over the first graphical object preceding selection of the second final emotion value; and
      in response to the second integrity falling below the threshold integrity, prompting the user to re-enter an emotion value via the graphical user interface.

2. The method of claim 1:
   wherein indexing the first emotion value through the spectrum of emotion values comprises:
      indexing the first emotion value forward through a set of integers from "1" through "10," inclusive, in response to a swipe input in a first direction into the graphical user interface; and
      indexing the first emotion value backward through the set of integers in response to a swipe input in a second direction into the graphical user interface, the second direction opposite the first direction; and
   wherein updating the first graphical object within the graphical user interface comprises updating the first graphic object to show a particular integer, from the set of integers, corresponding to a current first emotion value selected by the user through a sequence of swipe inputs into the graphical user interface.

3. The method of claim 2:
   wherein rendering the first graphical object within a graphical user interface comprises rendering a virtual sphere within the graphical user interface;
   wherein updating the first graphical object within the graphical user interface comprises rendering the virtual sphere in a first color and in a first amorphous form in response to selection of emotion values corresponding to higher content status of the user; and
   wherein updating the first graphical object within the graphical user interface comprises rendering the virtual sphere in a second color and in a second amorphous form in response to selection of emotion values corresponding to lesser content states of the user, the first color being warmer than the second color, and the second amorphous form being more solid than the first amorphous form.

4. The method of claim 2, wherein distributing the prompt to the external entity to monitor the user comprises:
   communicating a first prompt to monitor the user to a computing device associated with a therapist affiliated with the user in response to the first final emotion value equaling a first trigger value of "1"; and
   pushing a notification to interact with the user to a computing device associated with a known contact of the user in response to the first final emotion value equaling a second trigger value of "2."

5. The method of claim 1:
   wherein rendering the first graphical object within the graphical user interface comprises accessing an alternate digital keyboard within a native textual communication application executing on a mobile computing device and rendering the first graphical object within a message preview area of the alternate digital keyboard;
   wherein indexing the first emotion value assigned to the first graphical object comprises indexing the first emotion value represented on the first graphical object in response to and in a direction corresponding to a swipe input over the message preview area; and further comprising:
- transmitting the first graphical object to a recipient selected in the native textual communication application in response to receipt of a command at the native textual communication application to send the first graphical object to the recipient; and
- withholding the first final emotion value from the external entity in response to the first final emotion value differing from the trigger value.

6. The method of claim 5:
further comprising, prior to rendering the first graphical object within the graphical user interface, prompting the user to populate a support group with a set of contacts;
wherein accessing the alternate digital keyboard comprises accessing the alternate digital keyboard in replacement of an alphanumeric keyboard within a native text messaging application executing on the mobile computing device;
wherein distributing the prompt to the external entity comprises recording a first final emotion value selected by the user within the native text messaging application to a database of emotion values entered by the user and transmitting a form of the first final emotion value and an identifier of the user to the external entity comprising a mental health representative in response to the first final emotion value equaling the trigger value; and
further comprising communicating a form of the first final emotion value to a contact specified in the support group and distinct from the recipient in response to the first final emotion value exceeding the trigger value and a threshold intervention value exceeding the first final emotion value.

7. The method of claim 5:
wherein rendering the first graphical object within the graphical user interface comprises accessing an alternate digital keyboard within a native online social networking application executing on a mobile computing device and rendering the first graphical object within a message preview area of the alternate digital keyboard;
wherein updating the first graphical object to visually correspond to the first emotion value assigned to the first graphical object comprises updating a visual form of the first graphical object within the preview area to correspond to the first emotion value in response to the input into the graphical user interface;
further comprising posting the first graphical object to a social feed within an online social network in response to receipt of a command at the native online social networking application to post the first graphical object to the online social network; and
wherein distributing the prompt to the external entity comprises communicating the prompt to a contact previously affiliated with the user in response to the first final emotion value equaling the trigger value, the prompt directing the contact to the social feed.

8. The method of claim 1:
wherein rendering the first graphical object within the graphical user interface comprises rendering the first graphical object within a lock screen on a mobile computing device;
further comprising, in response to entry of a correct passcode into the lock screen on the mobile computing device, recording a first final emotion value selected by the user to a database of emotion values entered by the user; and
wherein distributing the prompt to the external entity comprises distributing the prompt to contact the user to the external entity in response to a first final emotion value, entered through the lock screen upon receipt of the correct passcode, equaling the trigger value.

9. The method of claim 1, further comprising gating access to an application through a computing device executing the graphical user interface until a first final emotion value is selected by the user and submitted through the graphical user interface.

10. The method of claim 9:
wherein gating access to the application comprises restricting access to an employer-issued checklist until the first final emotion value is selected by the user and submitted through the graphical user interface; and
wherein distributing the prompt to monitor the user to the external entity comprises communicating the first final emotion value and an identifier of the user to a mental health professional affiliated with the employer in response to the first final emotion value equaling the trigger value.

11. The method of claim 1:
further comprising receiving a first category label for the first final emotion value and storing the first final emotion value with the first category label;
wherein distributing the prompt to monitor the user to the external entity comprises prompting a member of a first support group affiliated with the user and associated with the first category label to contact the user in response to the first final emotion value equaling the trigger value for the first category label;
further comprising recording submission of a fourth emotion value through the graphical user interface, receiving a second category label different from the first category label for the fourth emotion value, and storing the fourth emotion value with the second category label; and
prompting a member of a second support group affiliated with the user and associated with the second category label to contact the user.

12. The method of claim 1:
wherein receiving the first category label for the first final emotion value comprises receiving the first category label corresponding to an overall emotional state of the user; and
wherein receiving the second category label for the fourth emotion value comprises receiving the second category label corresponding to one of: perceived financial comfort, perceived relationship comfort, perceived sleep quality, perceived anxiety level, perceived anger level, and perceived physical health of the user.

13. The method of claim 1:
further comprising storing a location of a computing device executing the graphical user interface at an approximate time the first final emotion value was entered by the user; and
wherein distributing the prompt to monitor the user to the external entity comprises dispatching an emergency responder to the location in response to the first final emotion value equaling the trigger value corresponding to a low state of contentment.

14. The method of claim 1, further comprising:
quantifying an emotional stability of the user based on the first final emotion value and emotion values previously entered by the user; and
customizing the trigger value for the user based on the emotional stability of the user.

15. A method for tracking and responding to mental health changes in a user, the method comprising:
during a first time:
rendering a first graphical object within a graphical user interface;
indexing a first emotion value assigned to the graphical object according to a direction of a swipe input over the graphical object within the graphical user interface;
updating a first color value and a first virtual viscosity of the first graphical object to correspond to the first emotion value assigned to the graphical object; and
in response to the first emotion value exceeding a first trigger value:
prompting the user to elect a first recipient from a contact list;
generating a first dynamic visual object, representing the first graphical object in the first color value and the first virtual viscosity corresponding to a first final emotion value selected by the user; and
transmitting the first dynamic visual object, in a first electronic notification, to the first recipient;
during a second time:
rendering a second graphical object within a graphical user interface;
indexing a second emotion value assigned to the second graphical object according to a direction of a swipe input over the graphical object within the graphical user interface;
updating a second color value and a second virtual viscosity of the second graphical object to correspond to the second emotion value assigned to the second graphical object; and
in response to the second final emotion value equaling a first trigger value:
selecting a second recipient in a support group including the user;
generating a second dynamic visual object, representing the second graphical object in the second color value and the second virtual viscosity corresponding to a second final emotion value selected by the user;
generating a second electronic notification comprising a prompt to contact the user; and
transmitting the second dynamic visual object, in a second electronic notification, to the second recipient; and
during a third time:
rendering a third graphical object within a graphical user interface;
indexing a third emotion value assigned to the third graphical object according to a direction of a swipe input over the graphical object within the graphical user interface;
updating a third color value and a third virtual viscosity of the graphical object to correspond to the third emotion value assigned to the third graphical object; and
in response to a third final emotion value equaling a second trigger value representing a less content state of the user than the first trigger value:
selecting a third recipient external to the support group;
generating a third dynamic visual object, representing the third graphical object in the color value and the third virtual viscosity corresponding to the third final emotion value selected by the user;
generating a third electronic notification comprising a prompt to contact the user; and
transmitting the third electronic notification to the third recipient.

16. The method of claim 15, wherein prompting a second recipient to contact the user comprises prompting the second recipient to send a song to a computing device affiliated with the user through a digital music service.

17. The method of claim 15, wherein prompting a second recipient to contact the user comprises sending, to the second recipient, a notification comprising a link to an online florist and a prompt to send flowers to the user.

18. The method of claim 15:
wherein indexing a first emotion value assigned to the graphical object comprises indexing the first emotion value forward through a set of integers from "1" through "10," inclusive, in response to a swipe input in a first direction into the graphical user interface and indexing the first emotion value backward through the set of integers in response to a swipe input in a second direction into the graphical user interface, the second direction opposite the first direction;
wherein distributing the dynamic visual object to the first recipient elected by the user comprises transmitting a digital file containing the dynamic visual object representing the first graphical object to the recipient through a private messaging channel;
wherein prompting the second recipient to contact the user comprises transmitting a prompt to the second recipient comprising a member of a support group associated with the user and other than the first recipient in response to the second final emotion value equaling the first trigger value contained within the set of integers; and
wherein distributing the third final emotion value to the mental health entity comprises notifying a mental health professional of the emotion value entered by the user in response to the third final emotion value equaling the second trigger value contained within the set of integers.

19. The method of claim 15:
wherein prompting the second recipient to contact the user comprises pushing a notification to the second recipient, specified in a support group affiliated with the user, to show concern for the user in response to the second final emotion value equaling the first trigger value; and
further comprising revealing a second emotion value, previously submitted by the second recipient through a second graphical user interface executing on a second computing device, to the user at the graphical user interface in response to receipt of the second final emotion value from the user.

* * * * *